United States Patent
Andersson et al.

(10) Patent No.: US 10,705,677 B2
(45) Date of Patent: Jul. 7, 2020

(54) METHOD AND SYSTEM FOR PLANNING IMPLANT COMPONENT POSITION

(71) Applicant: Ortoma AB, Gothenburg (SE)

(72) Inventors: Matts Andersson, Lerum (SE); Gunnar Flivik, Lund (SE)

(73) Assignee: Ortoma AB, Gothenburg (SE)

( * ) Notice: Subject to any disclaimer, the term of this patent is extended or adjusted under 35 U.S.C. 154(b) by 556 days.

(21) Appl. No.: 14/435,178

(22) PCT Filed: Oct. 17, 2013

(86) PCT No.: PCT/SE2013/051210
§ 371 (c)(1),
(2) Date: Apr. 13, 2015

(87) PCT Pub. No.: WO2014/062125
PCT Pub. Date: Apr. 24, 2014

(65) Prior Publication Data
US 2015/0265362 A1 Sep. 24, 2015

(30) Foreign Application Priority Data
Oct. 18, 2012 (SE) ...................................... 1251187

(51) Int. Cl.
*G06F 3/0481* (2013.01)
*G06F 3/0484* (2013.01)
(Continued)

(52) U.S. Cl.
CPC .......... *G06F 3/04815* (2013.01); *A61B 34/10* (2016.02); *G06F 3/04842* (2013.01);
(Continued)

(58) Field of Classification Search
CPC ... A61B 34/10; A61B 34/20; A61B 2034/102; G06F 3/04815; G06F 30/20;
(Continued)

(56) References Cited

U.S. PATENT DOCUMENTS

| 6,002,859 A | 12/1999 | DiGioia, III et al. |
| 7,388,972 B2 | 6/2008 | Kitson |
| (Continued) | | |

FOREIGN PATENT DOCUMENTS

| EP | 2175419 A2 | 4/2010 |
| WO | 2008139354 A2 | 11/2008 |
| WO | 2014062125 A3 | 4/2014 |

OTHER PUBLICATIONS

Hanson W A, Paul H A, Williamson W, Mittlestadt B: "Orthodock—An Image Driven Orthopaedic Surgical Planning System", Engineering in Medicine and Biology Society, 1990., Proceedings of the Twelfth Annual International Conference of the IEEE Philadelphia, PA, USA Nov. 1-4, 1990, pp. 1931-1932.; figures 1-4; Interactive docking system.

*Primary Examiner* — Juan C Ochoa
(74) *Attorney, Agent, or Firm* — Downs Rachlin Martin PLLC

(57) ABSTRACT

A method for planning an orthopedic procedure including positioning a virtual implant component relative to a 3D volume of scan data of a patient is disclosed. A 3D volume of scan data of a patient, which includes scan data of a bony anatomy of the patient, is provided. A first 2D view of scan data is generated from the 3D volume of the scan data, wherein the 2D view of scan data comprises a first portion of the bony anatomy. First positional information for the virtual implant component is defining relative to the first 2D view. A second 2D view of scan data is generated from the 3D volume of scan data, wherein the second 2D view of scan data is provided from the 3D volume of scan data at an angle relative to the first 2D view of scan data and comprises a second portion of the bony anatomy. Second positional information for the virtual implant component is defined relative to the second 2D view of scan data. 3D positional information for the virtual implant component relative the (Continued)

3D volume of scan data is provided based on the first positional information and the second positional information.

45 Claims, 10 Drawing Sheets

(51) Int. Cl.
*A61B 34/10* (2016.01)
*G06F 30/20* (2020.01)
*A61B 34/20* (2016.01)

(52) U.S. Cl.
CPC .............. *G06F 30/20* (2020.01); *A61B 34/20* (2016.02); *A61B 2034/102* (2016.02)

(58) Field of Classification Search
CPC ....... G06F 3/04842; G06T 7/70; G06T 19/00; G16H 30/40
USPC .............................................................. 703/1
See application file for complete search history.

(56) References Cited

U.S. PATENT DOCUMENTS

| | | | | |
|---|---|---|---|---|
| 7,660,623 B2 * | 2/2010 | Hunter | ................... | A61B 34/20 345/418 |
| 8,160,325 B2 * | 4/2012 | Zug | ........................... | A61F 2/46 382/128 |
| 8,160,326 B2 * | 4/2012 | Zug | ........................... | A61F 2/46 382/128 |
| 8,556,983 B2 * | 10/2013 | Bojarski | ............... | A61F 2/3859 606/86 R |
| 8,623,026 B2 * | 1/2014 | Wong | ................. | A61B 17/1703 29/592 |
| 8,634,618 B2 * | 1/2014 | Zug | ........................... | A61F 2/46 382/128 |
| 8,750,583 B2 * | 6/2014 | Zug | ........................... | A61F 2/46 382/128 |
| 9,020,788 B2 * | 4/2015 | Lang | ................... | A61F 2/30942 703/6 |
| 2002/0029047 A1 | 3/2002 | Bascle et al. | | |
| 2005/0004451 A1 | 1/2005 | Vilsmeier et al. | | |
| 2005/0203384 A1 * | 9/2005 | Sati | ........................ | A61B 6/547 600/426 |
| 2007/0055131 A1 | 3/2007 | Deinzer et al. | | |
| 2008/0077003 A1 | 3/2008 | Barth et al. | | |
| 2009/0318804 A1 * | 12/2009 | Avital | .................... | A61B 18/02 600/439 |
| 2010/0153081 A1 | 6/2010 | Bellettre et al. | | |
| 2011/0010187 A1 * | 1/2011 | Andersson | ............ | A61C 1/084 705/2 |

* cited by examiner

METHOD AND SYSTEM FOR PLANNING IMPLANT COMPONENT POSITION

FIELD OF THE INVENTION

This invention pertains in general to the field of planning an orthopedic procedure. More particularly, the invention relates to a method for planning an orthopedic procedure including positional information for a virtual implant component relative to a 3D volume of scan data of a patient. The positioning is based on providing positional information in multiple 2D views of scan data generated from the 3D volume of scan data that are combined to 3D positional information for the implant component relative the 3D volume of scan data.

BACKGROUND OF THE INVENTION

In orthopedic surgery damaged or worn joints can be replaced with prosthesis or implants, such as hip implants, knee implants, etc. The surgery may be planned to select the appropriate type, brand, size, etc. of the implant. This may be made using a technique referred to as templating. Conventionally, this was a manual technique, where pre-printed acetate sheets representing various configurations of implants where overlaid on top of physical x-ray images. Physical x-ray images are two-dimensional representations of a three-dimensional structure. Hence, no depth information is provided during the selection process. Furthermore, x-ray images are associated with magnifications and do not necessarily represent the true geometrical configuration of the patients bone. Thus, this technique can only be a rough guide to select the implant to be implanted. Hence, during the surgery, the surgeon still have to apply care to make sure that the implant selected fits the patient.

U.S. Pat. No. 7,388,972 discloses a templating method using digital x-ray images. In this method a reference object having a known size is scanned together with the patient and thus represented in the x-ray image. Then, the digital X-ray image can be scaled using the reference object. Even if this method may be more accurate than the manual templating technique using physical x-ray images, the scaling is an additional step that takes time and may not be accurate, whereby the selection of implant may be negatively affected. In an embodiment of the method, multiple x-ray images are used for selection of a knee prosthesis, wherein a first image, which is a medio-lateral view, is used for the selection of the femoral component of the implant, and a second image, which is an anterior-posterior view, is used for the selection of the tibial component. However, only one image is used for the selection of each component. Thus, this procedure is also a true two-dimensional planning procedure whereby lack of depth information may lead to the selection of a sub-optimal implant size. For example, an x-ray ray image obtained for a hip surgery is captured perpendicular to the pelvis. However, the femur head, femur neck and femur shaft extend are rotated relative pelvis, i.e. they are not parallel to the pelvis but rather extend from the acetabulum at an angle towards the x-ray image capture system. This has the consequence that true sizes of the femur head, femur neck, and femur shaft are not captured when the image is taken at the same time for the pelvis and femur. Therefore, a 2D image does not capture that the femur is rotated relative to the pelvis, and any templating that rely on such an image will be imprecise.

U.S. Pat. No. 6,002,859 discloses virtual simulation of position and thereby selection of the size of artificial components in three dimensions. Tomographic data is used to generate a three dimensional surface model of the skeletal geometric data. The geometric models of the artificial components can be used in conjunction with the surface model of the skeletal geometric data to determine an initial static estimate of the proper size of the artificial components to be implanted. The size and orientations of the implant component can be fully automated or manually controlled. Manual control is provided in three dimensions simultaneously over the selection of the implant components and the test positions in a biomechanical simulator.

US2010/0153081 discloses planning the position of an implant component relative bone in a coordinate space, such as relative to the base planning coordinate space of a CT volume of the bone. A graphical representation of the bone is in 3D, which can be generated by combining multiple segmented 2D slices, or by a 3D bone model. Multiple restriction axes are displayed for the positioning of the implement component in space. Hence, positioning is made in space and it is made in 3D relative to 3D models of the bone. Therefore, the technique disclosed therein suffers form the issues discussed below with regard to controlling position of virtual components in virtual space. Controlling the positioning in 3D is guided by the restriction axes, which are also provided in 3D space.

US2008/0077003 discloses various disadvantages with planning in 2D coordinates using 2D scan data, and suggests improved techniques by planning in 3D space. Objects, such as models of body parts, are generated and displayed on a monitor in 3D. The objects can be displayed in one or more screen views, i.e. viewing directions to the object. Hence, each screen window comprises a 3D model. The body part is presented in 3D with the object on the screen. The body part is moved and rotated around the virtual object. The respective 3D image data of the object and the body part are not altered during an automatic adaptation, but are visualized. Various three-dimensional representation formats are disclosed. If only 2D data exists for the object, 3D data can be generated from 2D data set based on known symmetries or prior knowledge. The body part is always available in 3D. The techniques disclosed herein are 3D planning, wherein the object as well as the body part are displayed in 3D. In some embodiments, the object is visualized in 2D, but the body part is always displayed in 3D. Hence this technique is a 3D planning technique that suffers form the issues discussed below with regard to controlling position of virtual components in virtual space.

Control of the position of virtual components in three dimensions in virtual space can be difficult for the person performing the pre-operative plan. All three degrees of freedom are manually controlled at the same time when the geometric models of the artificial component are used in conjunction with the surface model of the skeletal geometric data. Therefore, the selected position of the geometric model of the artificial component relative to the surface model of the skeletal geometric data may be imprecise, leading to selection of, e.g., sub-optimal implant. This may also affect any subsequent step that depends on the positioning of the geometric models of the artificial component, such as simulation of movement after selection of component, etc., and ultimately to inferior surgical outcome and patient safety and satisfaction.

Hence, an improved method for planning an orthopedic procedure would be advantageous and in particular allowing for improved precision, increased flexibility, planning efficiency, cost-effectiveness, and/or patient safety would be advantageous.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a method for planning an orthopedic procedure and positional information for a virtual implant component relative to a 3D volume of scan data of a patient according to the appended patent claims.

According to embodiments, a method for planning an orthopedic procedure comprises providing a 3D volume of scan data of a patient, which includes scan data of a bony anatomy of the patient; generating a first 2D view of scan data from the 3D volume of the scan data, wherein the 2D view of scan data may comprise a first a portion of the bony anatomy; defining relative to the first 2D view first positional information for the virtual implant component, such as relative to the first portion of the bony anatomy; generating a second 2D view of scan data from the 3D volume of scan data, wherein the second 2D view of scan data is provided from the 3D volume of scan data at an angle relative to the first 2D view of scan data and may comprises a second portion of the bony anatomy; defining relative to the second 2D view of scan data second positional information for the virtual implant component, such as relative to the second portion of the bony anatomy; and providing 3D positional information for the virtual implant component relative the 3D volume of scan data based on the first positional information and the second positional information.

The method may comprise adjusting the position of an object relative to the first 2D view of scan data for generating the first positional information. Additionally or alternatively, the method may comprise adjusting the position of an object relative to the second 2D view of scan data for generating the second positional information. The adjusting may be locked to adjustment in a single dimension in each 2D view of scan data.

The method may comprise displaying a third 2D view of scan data generated from the 3D volume of scan data. The third 2D view of scan data may be provided from the 3D volume of scan data at an angle relative to the first 2D view of scan data and relative to the second 2D view of scan data. The third 2D view of scan data may comprise a third portion of the bony anatomy. Third positional information for the virtual implant component may be defined relative to the third 2D view of scan data, such as relative to the third portion of the bony anatomy. 3D positional information for the virtual implant component relative the 3D volume of scan data may be provided by the first positional information, the second positional information, and the third positional information.

The method may comprise displaying a 3D representation the virtual implant component in a position defined by the first and second positional information. A position adjustment object may be displayed and may be associated with the virtual implant component and may be moveable in a single dimension at the time, wherein each dimension is parallel to at least one of the first and the second 2D views of scan data.

Defining first and second positional information for the virtual implant component may comprise defining positional information for at least one of an affected femoral head, affected femoral shaft, unaffected femoral head, unaffected femoral shaft, a cup of the virtual implant, a stem of the virtual implant, and a knee implant.

The method may comprise dividing the 3D volume of scan data into a first 3D sub-volume of scan data and a second sub-volume of scan data based on the first and second positional information, and optionally also based on at least of a section of the virtual implant component. The method may comprise displaying a first virtual implant component in a position relative to the 3D scan data based on the first and the second positional information, and a second virtual implant component, which is a virtual representation of the position of an actual implant relative to the actual bony anatomy of the patient.

The method may comprise exporting navigational data based on the first and second positional information to a navigation unit for guiding the position of an actual implant relative to actual bony anatomy of the patient.

The method may comprise generating the first 2D view and the second 2D view, and optionally the third 2D view, using reformatting techniques, e.g. projection methods such as maximum intensity projection and/or minimum intensity projection, to provide at least one of reformatted and reconstructed slices. The 2D views may comprise at least one of images reformatted and reconstructed from the 3D volume of scan data. Optionally the 2D views may comprise grey values displayed as pixel data obtained from one or several voxels of the 3D volume of scan data. Optionally or additionally, the method may comprise generating the first 2D view and the second 2D view, and optionally the third 2D view, at an angle relative to each other to be orthogonal.

The method may comprise defining the first positional information and the second positional information, and optionally the third positional information, for the virtual implant component restricted to maximum two degrees of freedom, optionally to a single degree of freedom, for at least one of the first positional information and the second positional information, and optionally the third positional information.

The method may comprise defining the first positional information in the dimensions of the first 2D view and defining the second positional information in the dimensions of the second 2D view, and optionally defining the third positional information in the dimensions of the third 2D view.

The method may comprise displaying each of the first 2D view, the second 2D view, and optionally the third 2D view separately, such as in different screen windows but at the same time.

The method may comprise adjusting at least one of the first positional information relative to the first 2D view and the second positional information relative to the second 2D view, and optionally the third positional information relative to the third 2D view. Hence, the first, second, and third positional information and thereby the position of virtual implant component, respectively, can be adjusted relative to the first portion, the second portion, and the third portion, respectively, of the bony anatomy.

The method may comprise the adjusting at least one of the first positional information and the second positional information, and optionally the third positional information, for the virtual implant component guided by an offset for an affected anatomy relative an unaffected anatomy.

The method may comprise defining each of the first positional information and the second positional information, and optionally the third positional information, to comprise coordinate information in one or two dimensions, wherein the combination of the first positional information and the second positional information, and optionally the third positional information, comprises coordinate information in three different dimensions.

According to embodiments, a computer system comprises a programmable device adapted to perform the method according to embodiments of the invention.

According to embodiments, a computer program product stored on a computer readable medium, comprising: computer readable program code segments for causing a computer to execute the method according to embodiments of the invention.

Further embodiments of the invention are defined in the dependent claims,

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 5a-10c are front views of a display comprising various 2D views for positioning of an implant component in 3D space.

DESCRIPTION OF EMBODIMENTS

Figure 1:
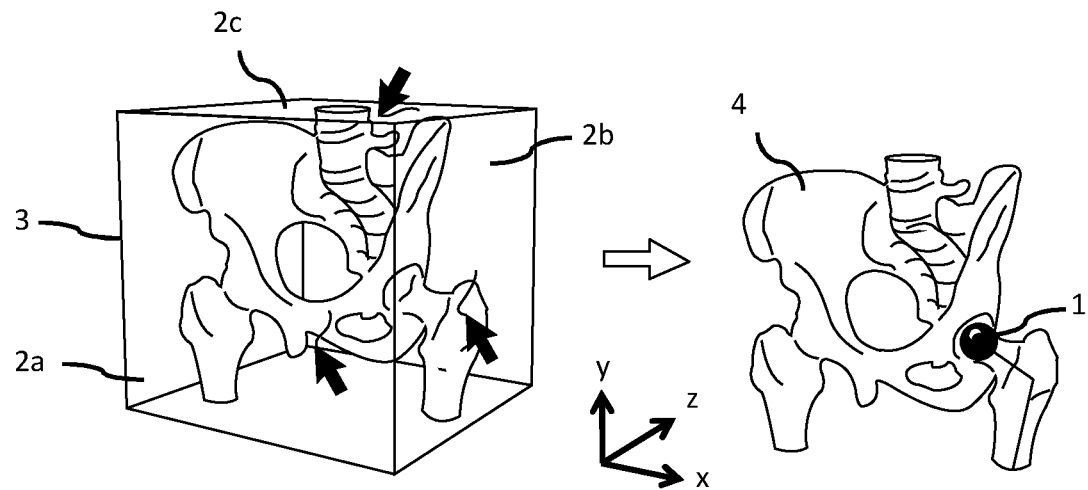
FIG. 1 is a perspective view of a 3D volume of data and three 2D views generated therefrom, and an implant component positioned in 3D relative to the scan data rendered in 3D.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on embodiments of the present invention applicable for planning an orthopedic procedure. The method includes positioning a virtual implant component relative to a 3D volume of scan data of a patient. Embodiments of the invention will be described in the following with regard to planning a hip replacement procedure using a hip implant comprising an acetabular cup component and a femoral stem component. However, it will be appreciated that the invention is not limited to this application but may be applied to many other orthopedic procedures, such as joint implant procedures, e.g. a knee implant procedure, an ankle implant procedure etc. wherein one or several implant components may be included in the procedure. For example, positioning a virtual implant component may comprise defining positional information for at least one of an affected femoral head, affected femoral shaft, unaffected femoral head, unaffected femoral shaft, a cup of a virtual implant, and a stem of a virtual implant.

Embodiments of the invention will be described with reference to the method illustrated in FIG. 3. Furthermore, individual steps of the method will be further described by reference to FIGS. 5a-10 including two-dimensional (2D) views generated from of a three-dimensional (3D) volume of scan data. First, an overview of the method according to embodiments of the invention will be provided, followed by a more detailed description of individual steps. Reference will be made to various implant components, such as cup, stem, joint, etc. Since the planning is made in virtual space, it is implicit that whenever reference is made to such an implant component, this is a virtual implant component wherein the position and positional information is planned in virtual space.

Figure 2:
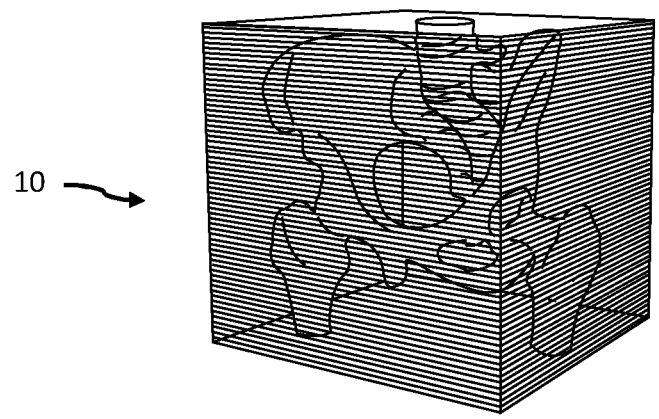
FIG. 2 is a perspective view of scan data.

FIG. 1 illustrates embodiments of the invention, wherein planning the position of a virtual implant component 1 is done by providing positional information for the implant component 1 in multiple 2D views 2a, 2b, 2c of scan data relative to a 3D volume 3 of scan data. The 2D views 2a, 2b, 2c may be images reformatted from the 3D volume 3. Furthermore, the 2D views 2a, 2b, 2c may be generated at an angle relative to each other, such as to be orthogonal, as is illustrated in FIG. 1. Hence, by providing positional information in a first and second dimension, such as along an x-axis and y-axis, relative to a first 2D view 2a and additional positional information in a third dimension, such as along the z-axis, relative to a second 2D 2b view while maintaining the position from the first view 2 as the implant component 1 can be positioned in 3D space relative to the 3D volume 3 of scan data. The position of the implant component 1 in 3D space and relative to the 3D volume 3 of scan data may be provided based on positional information defined using multiple 2D views of scan data 2a, 2b, 2c. Hence, positioning relative the scan data is done in 3D space using multiple 2D views 2a, 2b, 2c generated at an angle relative to each other and from the same volume 3 of scan data. In other embodiments, positioning of the implant component is limited to one dimension in a single 2D view 2a, 2b, 2c, wherein positioning in 3D space may be provided using at least three 2D views generated from the same 3D volume of scan data and at an angle relative to each other. The 2D views 2a, 2b, 2c may e.g. comprise at least two of a sagittal view, a coronal or frontal view, and a horizontal or transaxial view. FIG. 1 illustrates planes of a volume at the same time for illustrative purposes. According to the method of embodiments of the invention, each plane or 2D view 2a, 2b, 2c are displayed separately, wherein the various dimensions associated with each view is defined for each view at the time. When defined, the implant component 1 may be displayed in 3D together with the scan data rendered in 3D, such the 3D bony anatomy 4 illustrated to the right in FIG. 1. The 3D volume 3 of scan data 10 may comprise tomographic scan data, such as CT or MR scan data. The 2D views of scan data may be generated using reconstruction, reformatting, and display techniques based on a stack of axial slices, such as illustrated in FIG. 2. According to embodiments of the invention, each 2D view may comprise an image. The 2D views are generated to resemble a traditional X-ray image. However, due to the combination of multiple 2D views resembling traditional x-ray images generated from the same 3D volume of scan data, a third dimension can be added to the planning while the surgeon still can access the type of data he/she is most familiar with. Since the third dimension is added to the planning, it is possible to consider the rotation effect, i.e. such as that the femur head, femur neck, and femur shaft are rotated relative to pelvis while the image scan data is captured. Hence, a planning done in a first 2D image can be adjusted in a second 2D image, wherein the rotation effect can be considered and a more accurate planning performed.

In order to generate the 2D views, reformatting techniques, e.g. projection methods such as maximum intensity projection and/or minimum intensity projection, may be used to provide reformatted and/or reconstructed slices. Hence, the 2D views may comprise images reformatted and/or reconstructed from 3D volume of scan data. Hence, the 2D views may comprise grey values, displayed as pixel data obtained from a voxel of the 3D volume of scan data.

Providing positional information for the implant component is restricted to maximum two-degrees of freedom, in some embodiments to a single degree of freedom. Hence, control of the positioning is enhanced, which in turn leads to improved end position of the implant component compared to prior art solutions. Hence, any subsequent procedure that makes use of the end position of the implant component will thus be enhanced, leading to improved patient safety and satisfaction. For example, the end position may according to embodiments of the invention be used for the generating sub-volumes of scan data, which may be used for volumetric rendering of the scan data and the sub-volumes of scan data. The volumetrically rendered data may e.g. be used for simulating movement of bone structures to which the implant component is to be attached. With improved positioning of the implant component, improved simulation of movement and thus outcome of the surgery may be obtained. In other embodiments, the position of the implant component may be used for generation of a surgical template, which may be used for cutting bone or positioning the actual implant component during surgery. Consequently, the more accurate position of the virtual implant component relative the scan data the more accurate positioning of the surgical template relative the bone of the patient or the actual implant and thus more predictable surgical outcome. Improved control of the positioning in 3D space also provides for less corrections of the position of the implant component during the planning procedure, wherein the planning procedure as such may be more efficient, both in terms of time and computational power.

Figure 3:
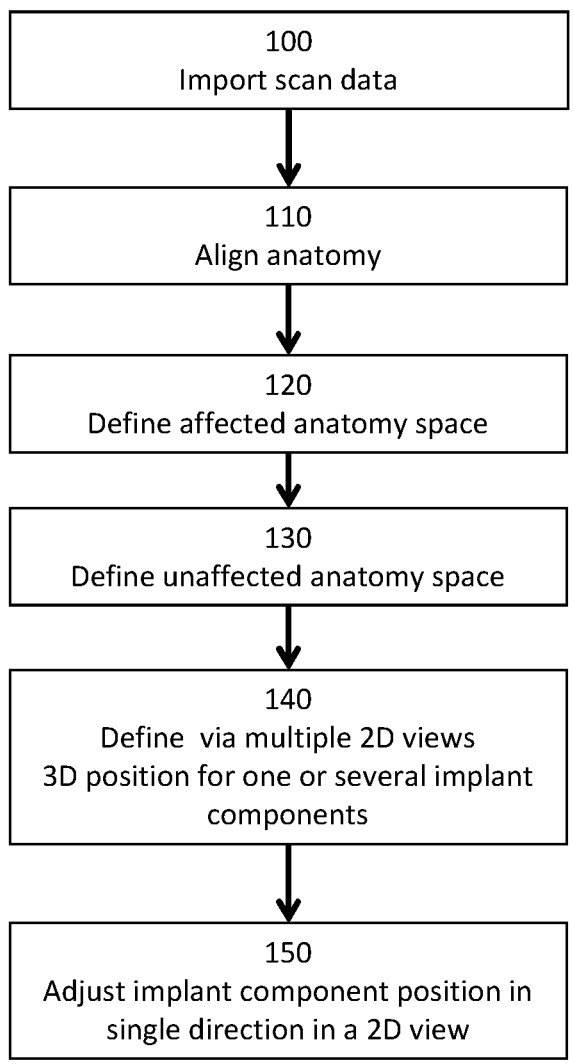
FIG. 3 is a flow-chart of a method according to embodiments of the invention.

FIG. 3 illustrates steps according to embodiments of the invention. In step 100, the 3D volume of scan data is provided. This may e.g. be provided by importing the scan data into the planning software, where the positioning of the implant component relative the scan data is performed. As is illustrated in FIG. 2, the scan data 10 may e.g. comprise DICOM data generated using CT or MR, and be imported from a storage medium, such as a DVD, hard disc, SSD memory, via a network, such as an intranet or internet to a which a PACS (Picture Archiving, and Communication System) is connected, etc. Providing the scan data 10 may also comprise defining a region of interest, such as to limit the scan data and reduce the requirements on the processor, graphic card, memory, etc. Also, providing the scan data may also comprising setting the sampling direction for generating the 2D views, which e.g. may be set when a region of interest is selected. The scan data 10 may comprise a set of 2D slices, that may be reconstructed into 3D volume of scan data, such as using multiplanar reconstruction, wherein a volume is built by stacking the axial slices. Alternatively or additionally, projection methods such as maximum intensity projection and/or minimum intensity projection may be used to provide reconstructed slices and a volume of data.

In step 110, the scan data may be aligned with the sampling directions of the 2D views. This step is not provided for in all embodiments. It may be useful, e.g. when measurements are made in the 2D views, such as based on orientation objects positioned in the 2D views by the person performing the planning. For this purpose, the horizontal line, the median plane, the horizontal orientation, and the vertical orientation may be adjusted. Hence, based on the planning, measurements between an affected side and an unaffected side before and after the expected outcome of the surgery may be provided, as will be further discussed below. Aligning the scan data with the biomechanical zero of the planning system, such as to planning planes thereof, e.g. provides for assessing the rotation of the femur relative to pelvis, e.g. from multiple angles. Rotation effects that are associated with 2D planning systems can be considered according to embodiments of the invention, which contributes to a more accurate planning. Furthermore, embodiments of the invention provide for aligning anatomy that has not been captured at appropriate angles relative to the image capturing system for calculating offsets. This also provides for more accurate calculations of offsets.

In step 120, the affected anatomy space is defined. This may be made in 3D space using multiple 2D views of the scan data. In a first 2D view, an affected area may be indicated by positioning a first affected area position object, such as a circle, relative to the 2D view of scan data. In a second 2D view, the affected area may be indicated by positioning a second affected area position object, such as a circle or a line, relative to the 2D view of scan data. The positions of the first and the second affected area position indicators can be adjusted in maximum two dimensions each, and are in some embodiments limited to adjustment in a single degree of freedom each, relative any 2D view of scan data. Together, optionally also using a third affected area position indicator positioned in a third 2D view of scan data, the affected anatomy space is indicated in 3D space. In some embodiments, the first, second, and third affected area position indicators are different 2D views of a single 3D affected area position indicator. The coordinates of each position object provide position information in one or two dimensions, such as any one or two of x-/y-/z-dimensions. The coordinates of the implant component in the x-dimension, y-dimension, and the z-dimension, may be based on the combination of the coordinates of the position objects positioned in the 2d views 2a, 2b, 2c, as is illustrated in FIG. 1.

In step 130, the unaffected anatomy space is defined. This step is optional and may be provided for obtaining measurements, such as for offsets between the affected and unaffected anatomy space before surgery and after the surgery when the actual implant component subject to the planning has replaced the affected anatomy space. The affected anatomy space can be indicated using the same steps as described with regard to step 120 and using first, second, and third unaffected position objects to provide positional information for the implant component.

In step 140, the implant component is positioned in 3D space relative to the 3D volume of scan data using multiple 2D views of the scan data. Positional information for the implant component can be provided based on the first and second affected area, and optionally third, position indicators. The implant component can be a 3D virtual object. The 3D virtual object can be a 3D template for deciding the appropriate implant size. Hence, planning in three dimensions provides for 3D templating, which can be more accurate than using a 2D templating technique. This provides also for rotating the template as well as the bony anatomy and thus accurate planning. Furthermore, planning in 3D with multiple 2D views where the 3D implant component or object are viewed together with the 2D views provides for more accurate planning. For example, in planning systems wherein the bony anatomy is rendered using 3D volume rendering techniques together with 3D templates, the tomographic data is lost and positioning of the template is challenging, which are issues improved with embodiments of the invention. This is for example the case according to the method disclosed in US2008/0077003.

In step 150, the position if the implant component can be adjusted. For example, at least one of first positional information, second positional information, and third positional information for the implant component can be adjusted relative to a first 2D view, a second 2D view and a third 2D view, respectively, and thereby relative to the affected anatomy. In some embodiments, adjustment of the position may be provided in a plane, i.e. in two dimensions. In other embodiments, adjustment of the implant component position is locked to a single direction or dimension, i.e. a single degree of freedom. Hence, for some implant components, repositioning of the implant component in three dimensions in 3D space is performed in three separate 2D views. The adjustment of the position of the implant component may be guided by the offset for the affected anatomy and the unaffected anatomy, i.e. the offset for the affected anatomy relative the unaffected anatomy, wherein the affected anatomy and the unaffected anatomy may be corresponding anatomies, such as hip joints on each side of the body wherein only one of the hip joints is affected. If offset information for the implant component and the unaffected anatomy is also provided, the position of the implant component may be adjusted such that the offset is optimal from a surgical perspective.

Figure 4:
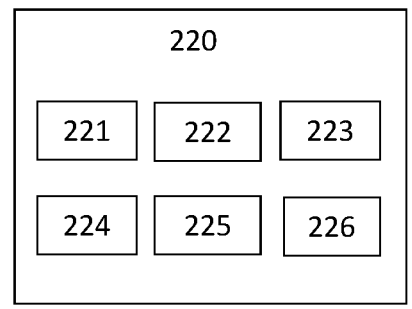
FIG. 4 is a block diagram of a planning station according to embodiments of the invention.

FIG. 4 illustrates a computer system 220, in which the scan data may be imported and the surgery planned. The computer system 220 may also be used during surgery as the planning unit wherein the positional information for the implant component may also be accessed to guide the surgeon visibly via a display. Alternatively, a separate planning unit is provided during surgery, wherein the computer system 220 is used during planning does not need capability to access the current position data of the surgical object. The computer system 220 comprises a CPU or data processing unit 221, one or several memories 222, a communication unit 223, a reading unit 224 for reading the scan data, an input device 225, such as a mouse and/or a keyboard, and an output unit 226, such as a display in which various displays and views described below may be rendered. Furthermore, the computer system 220 may comprise computer software for performing a pre-operative plan, such as planning using multiple 2D views of scan data as will be described below. The computer software may comprise a CAD system, wherein the scan data can be rendered, such as a 3D model of the surgical object or the 3D volume of scan data, and/or multiple 2D views of scan data, such as MRI or CT data, generated from the 3D volume of scan data. The 3D model of the surgical object and the 2D views of scan data may also be rendered at the same time and be partially overlaid in order to increase the information. The CAD system may be based on a general purpose CAD system, such as 3ds Max from Autodesk®. Once the scan data has been imported, a 3D model of the surgical object 11 can be provided. The 3D model may e.g. be a 3D surface model or a point cloud created using a 3D graphics technology.

The steps of FIG. 3 will now be described in more detail by reference to FIGS. 5a-10. Importing volumetric scan data into a planning software is generally known, and step 100 will therefore not be described in more detail herein. Importing volumetric scan data may comprise providing a 3D volume of scan data of a patient, which includes scan data of a bony anatomy of the patient. The 3D volume of scan data may also be provided by first importing a volume of scan data, which then is reduced by defining a region of interest in one or multiple 2D views of the scan data. In FIGS. 5a-10, the bony anatomy is shown in white, whereas soft tissues are cross-hatched. However, in a real display, the scan data may comprise any type of scan data, such as represented by grey values including both soft-tissue and bone-tissue, such as according to Hounsfield scale.

The 2D views may be displayed at the same time, as is illustrated in FIGS. 5a-10, wherein a larger 2D view is presented one side of the display, and two smaller views presented in a column on the other side of the display. In some embodiments, providing positional information is only activated in one of the 2D views at the time. Activating a 2D view for providing positional information may be made by activating the input device 225 while a 2D view is indicated, such as indicating by positioning a cursor operated via mouse, in the 2D view and activating by clicking an activation button of the mouse. Activating the 2D view may also shift the position of the activated 2D view on the display. Hence, an activated 2D view may in some embodiments shift position from right to left on the display, or vice versa, and additionally or alternatively from smaller to larger in size. In the embodiments of FIGS. 5a-10, an activated 2D view is larger in size and presented to the left on the display. This is only one possible layout, and it should be understood that other embodiments may have different layouts on the display in which the 2D views are presented.

Figure 5A:
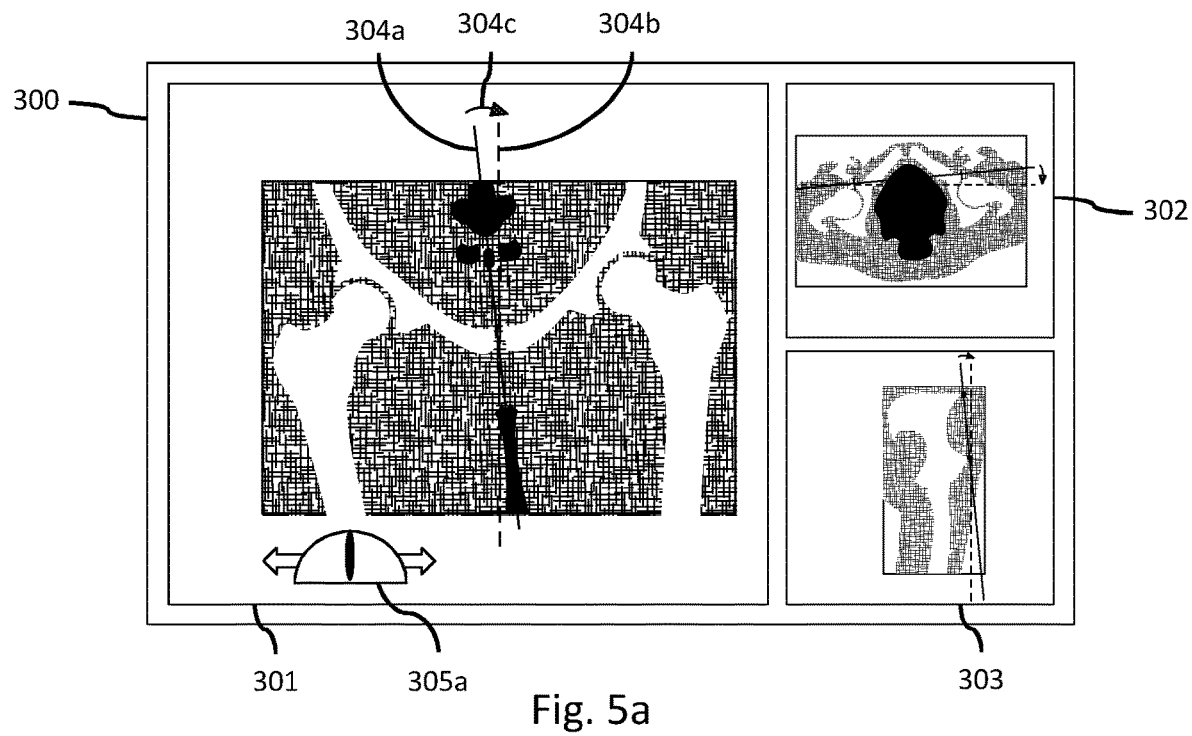
Figure 5B:
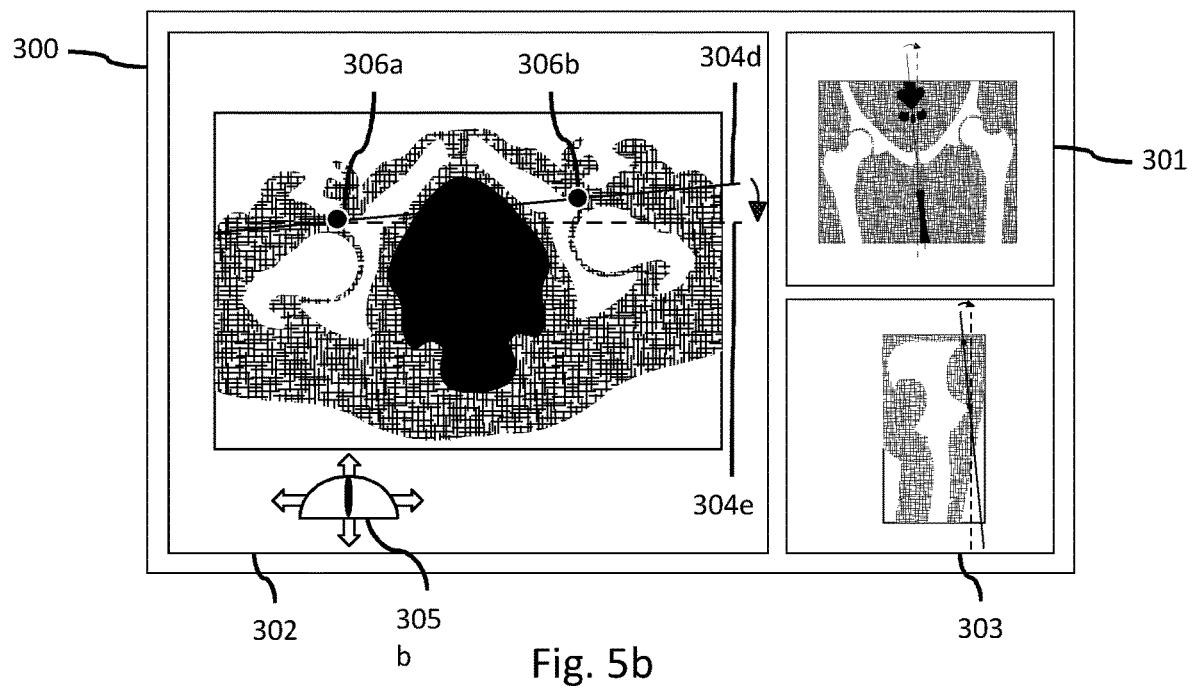

FIGS. 5a-5b further illustrate step 110 of FIG. 1, wherein the anatomy or scan data is aligned with the 2D views, and thus the planes in which measurements may be provided. On a display 300 is displayed a first 2D view 301 of scan data, a second 2D view 302 of scan data, and a third view 303 of scan data. The first, second, and third 2D views 301, 302, 303 are generated from the 3D volume of the scan data. The first 2D view 301 is in this embodiment a coronal or frontal view, of the scan data. The second 2D view 302 is in this embodiment a horizontal or transaxial view of the scan data. The third 2D view 303 is in this embodiment a sagittal view of the scan data. The first 2D view 301 comprises a first portion of the bony anatomy, such as any portion included in the coronal view. The second 2D view 302 comprises a second portion of the bony anatomy, such as any portion included in the horizontal view. The third 2D view 303 comprises a third portion of the bony anatomy, such as any portion included in the horizontal view. The second 2D view 302 is provided from the 3D volume of scan data at an angle relative to the first 2D view 301 of scan data and comprises a second portion of the bony anatomy.

In some embodiments, the third 2D view 303 of scan data is generated from the 3D volume of scan data. The third 2D view 303 may provided from the 3D volume of scan data at an angle relative to the first 2D view 301 of scan data and the second 2D view 302 of scan data. The third 2D view 302 of scan data may comprise a third portion of the bony anatomy. This provides for defining positional information in a single dimension at the time, one in each 2D view 301, 302, 302 of scan data, and still be able to define positional information for the implant component in three dimensions relative to the 3D volume of scan data. Hence, third positional information for the virtual implant component may be defined relative to the third 2D view 303. Then, 3D positional information for the implant component relative the 3D volume of scan data may be provided based on the first positional information provided relative to the first 2D view 301 of scan data, the second positional information provided relative to the second 2D view 302 of scan data, and the third positional information provided relative to the third 2D view 303 of scan data.

In order to align the anatomy included in the scan data the coronal plane of the 3D volume of scan data may be aligned with the coronal planning plane of the first 2D view 301 by adjusting the horizontal line and median plane. In the first 2D view 301, the coronal plane may be aligned, such as the horizontal line (not illustrated) indicated by a line between two circles, and the medial plane, with the scan data. The positional information may comprise position of orientation objects, such as a line, rectangle or a circle. In FIG. 5a, the scan data comprises bony anatomy of a pelvis. In order to align the bony anatomy with planning planes of the 2D views, such as the coronal plane, the median plane is indicated with a line 304a. The median plane of the planning plane in which further planning is made is indicated with a dotted line 304b. The median plane of the scan data is aligned with the median plane of the planning plane 304b, as is indicated with the curved arrow 304c. Positioning of the orientation object for the median plane may be initiated by selecting a median plane function of the planning program. By positioning the orientation object for the median plane relative to the 2D view of scan data, an affected and unaffected side may be indicated. This may be used to calculating offsets. In the first 2D view 301, adjustment of the position of orientation object, here the line indicating the median plane, is limited to adjustment in one dimension. In this embodiment, the orientation object, here the line for the medial plane, it is limited to re-position sideways, which is indicated by the direction indicator 305a, which is two-way direction indicator in the form of a stylized mouse with a two-way arrow. Adjusting the coronal plane may thus be done relative to a single 2D view of scan data and wherein adjustment is limited to a single dimension.

Next in the planning process is to adjust the transverse plane of the 3D volume of scan data with the sagittal planning plane and/or the second 2D view 302 by adjusting the horizontal orientation of the pelvis. This may be done by activating the second 2D view 302, which may be a horizontal view, and adjusting the horizontal orientation. FIG. 5b illustrates the state of the display 300 after the second 2D view 302 has been activated. In this state, the first 2D view 301 has been de-activated and it is no long possible to define any positional information relative to this view unless it is activated again. Instead, the second 2D view 302 has been activated. Second positional information may now be provided relative to the second 2D view 302. In this view, positional information in the form of the position of second orientation objects 306a, 306b, here shaped as circles, are indicated at appropriate positions of the pelvis, the positions of which are generally know to the skilled surgeon performing the planning. Between the orientation objects 306a, 306b is a line generated, which indicates the horizontal orientation. Once both second orientation objects 306a, 306b are placed, the scan data is aligned with the 2D horizontal planning plane, and may be used for the generation of horizontal offsets after subsequent planning steps. The horizontal line of the scan data 304d is indicated in FIG. 5b with a line, and the horizontal line of the planning plane with a dotted line 304e. Once, the horizontal line of the scan data has been indicated, it can be aligned with the horizontal line of the planning plane, which is predefined. Adjusting the positional information for the horizontal plane it is limited to re-position in the plane, i.e. in two dimensions, which is indicated by the direction indicator 305b, which is a four-way direction indicator in the form of a stylized mouse with a four-way arrow. In the third 2D view 303, the sagittal plane of the scan data may be aligned with the sagittal planning plane of the third 2D view 303 by adjusting the vertical orientation of the pelvis. Activation of this 2D view is not illustrated in detail, but may be made in the same way as for providing positional information for the horizontal orientation relative the transverse plane illustrated in FIG. 3b. Adjusting the positional information for the vertical orientation relative the sagittal plane it is limited to re-position in the plane, i.e. in two dimensions, or in one dimension.

Adjusting the bony anatomy of the scan data relative to the planning planes of the 2D views via multiple 2D views 301, 302, 303, provides 3D positional information that may be used for providing positional information for the virtual implant component relative the 3D volume of scan data. The 3D positional information for the implant component relative to the 3D volume of scan data may be based on the first positional information and the second positional information, and optionally by the third positional information, for the orientation objects.

FIGS. 6a-6d further illustrate step 120 of FIG. 3, wherein a first portion of the affected anatomy space is indicated. Positional information for an affected femur head is provided in a first 2D view 401 and a second 2D view 402. The first 2D view 401 is generated from the 3D volume of the scan data and is in this embodiment a coronal view of a first portion of the bony anatomy of the scan data, as has been described with regard to FIG. 5a-5b. The second 2D view 402 is generated from the 3D volume of scan data and is in this embodiment a horizontal view of a second portion of the body anatomy of the scan data. The second 2D view 402 is provided from the 3D volume of scan data at an angle relative to the first 2D view 401 of scan data. In this embodiment, a third 2D view 403, which is a sagittal view of a third portion of the bony anatomy of the scan data, is generated from the 3D volume of scan data. The third 2D view 403 is provided from the 3D volume of scan data at an angle relative to the first 2D view of scan data 401 and relative to the second 2D view of scan data 402. The first 2D view 401, the second 2D view 402 and the third 2D view 403 may be orthogonal relative to each other. Activation of the first 2D view 401, the second 2D view 402 and the third 2D view 403 may be done in the same way as described with regard to FIGS. 5a-5b.

In this embodiment, a position object 404 comprises a sphere, which is represented in each 2D view as a circle. The position object 404 can be introduced into the first 2D view by first initiating a function for defining a first portion of the affected anatomy, in this embodiment the affected femur head. The position of the position object 404 relative to the 3D volume of scan data provides positional information for the implant component. In this embodiment, the implant component is a cup for a hip implant. Once the function is initiated, the position object can be positioned using the input device in the active 2D view, which may be the first 2D view 401, the second 2D view 402, or the third 2D view 403. When the position object has been introduced into one of the 2D views, it may appear in the other 2D views, e.g. if it is a three dimensional object and it is represented in the different 2D views by a 2D object in each view. Hence, the position object 404 may first be introduced in one of the 2D views 401, 402, 403, and then the position of the position object 404 may be adjusted in any of the 2D views 401, 402, 403. Introducing the position object in one of the 2D views 401, 402, 403 provides first positional information, and adjusting the position in any of the other 2D views provides second positional information. The first and/or the second positional information may comprise coordinate information in one or two dimensions. Hence, if the first and the second positional information together only comprises information in two dimensions, positional information in a third dimension may be necessary from a third 2D view. Together, the first positional information, the second positional information, and optionally the third positional information may provide coordinate information in three dimensions for the position object relative to the 3D volume of scan data.

Figure 6A:
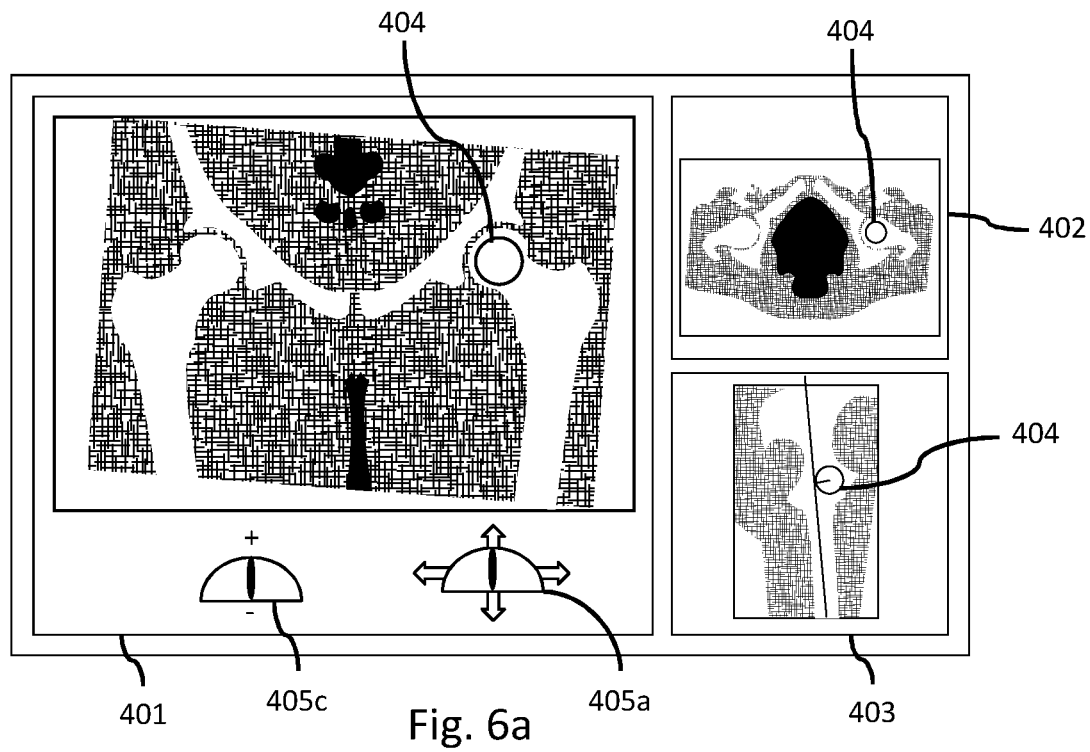
Figure 6B:
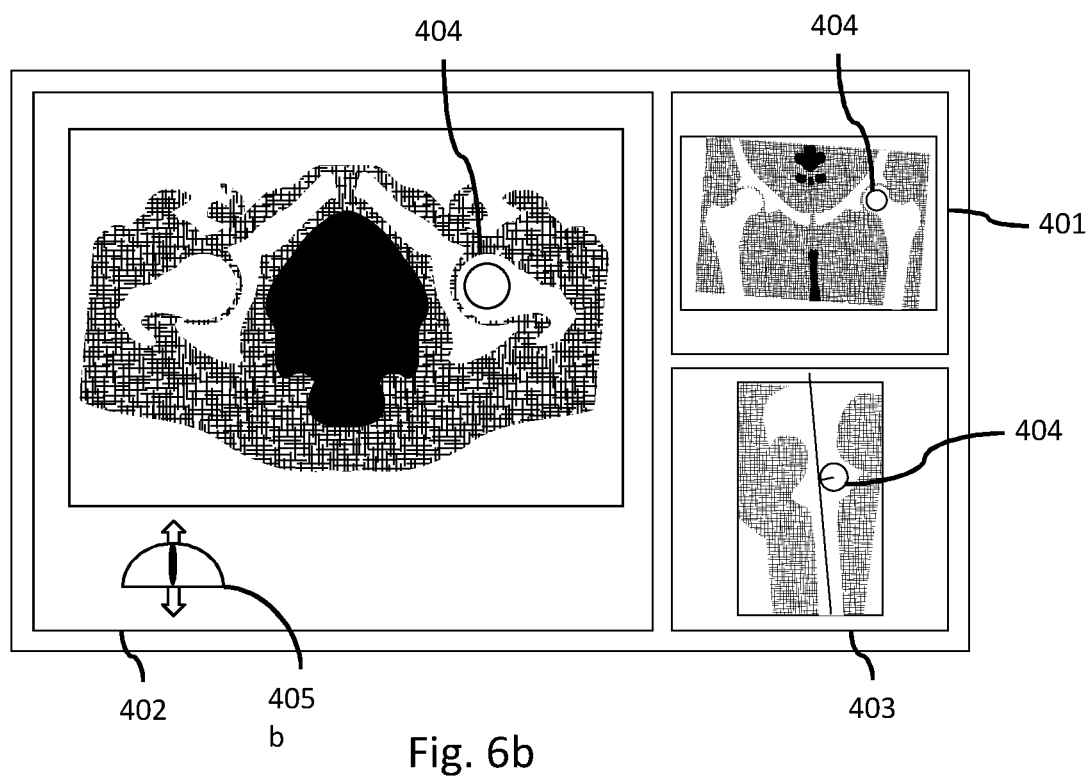

The position of the position object 404 can be adjusted in 3D space by adjusting its position in at least two of the 2D views 401, 402, 403, optionally three of the 2D views 401, 402, 403, depending on the degrees of freedom for adjusting its position. In the embodiment of FIGS. 6a-6b, the position of the position object can be adjusted in two dimensions in the first 2D view 401 and in only one dimension in the second 2D view 402, which is indicated by a four-way direction indicator 405a, and a two-way direction indicator 405b, respectively. The size of the position object 404 may be adjusted using the input device, such as scrolling the scroll wheel of a mouse, which is indicated by a size indicator 405c. The size indicator is in this embodiment a stylized mouse with associated "+" and "−" indicating the size can be enlarged ("+") and reduced ("−"). The position of the position object 404 may also be adjusted in the third 2D view if desired. However, in order to adjust the position in three dimensions, this is not necessary but may be desired for more accurate positioning. Hence, when the position of the position object 404 has been adjusted, the affected anatomy has been defined. The coordinates of the position object defined in multiple 2D views in the x-dimension, y-dimension, and z-dimension provide the x/y/z coordinates for the affected anatomy space.

Figure 6C:
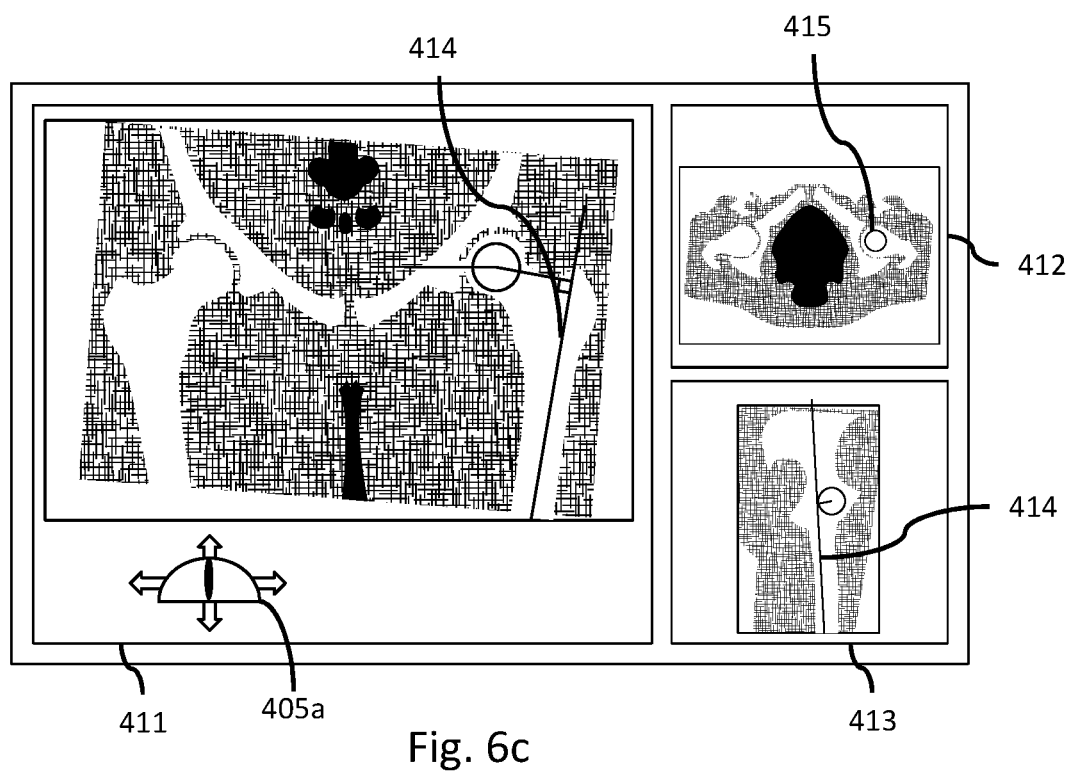
Figure 6D:
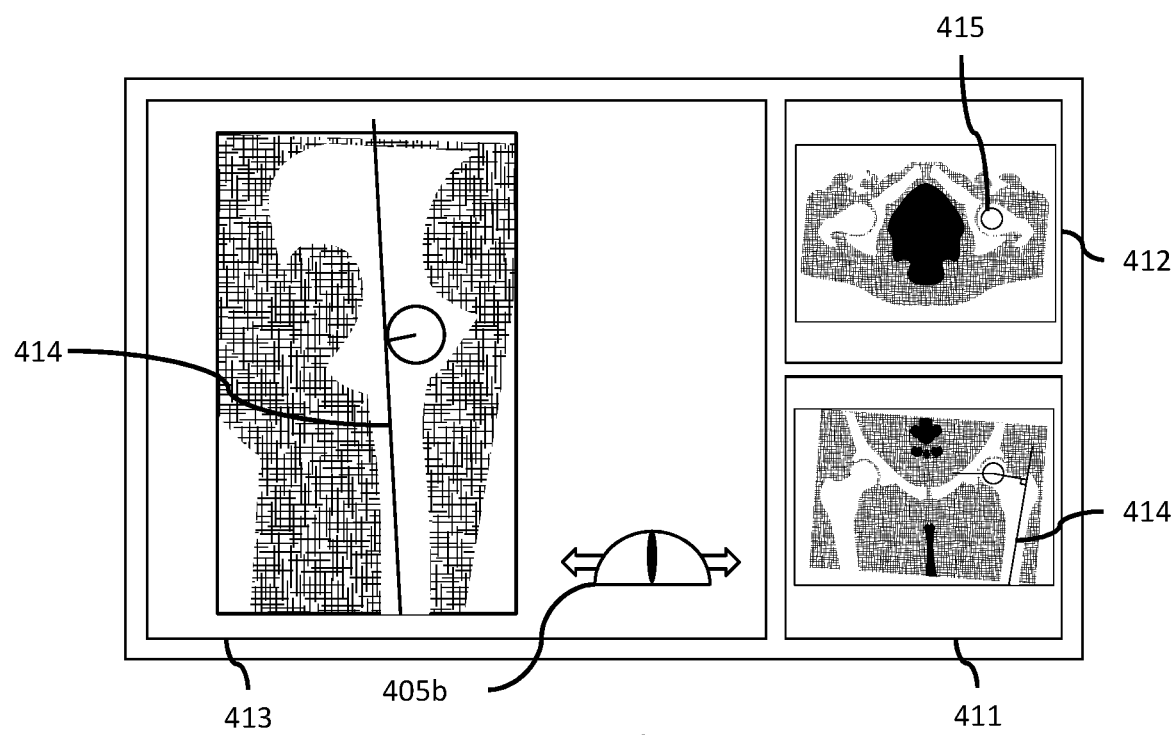

FIGS. 6c-6d further illustrate step 120 of FIG. 3, wherein the second portion of the affected anatomy space is indicated. Positional information for an affected femur shaft is provided in a first 2D view 411 and a second 2D view 412. The first 2D view 411 is generated from the 3D volume of the scan data and is in this embodiment a coronal view of a first portion of the bony anatomy of the scan data, as has been described with regard to FIG. 5a-5b. The second 2D view 412 is generated from the 3D volume of scan data and is in this embodiment a horizontal view of a second portion of the body anatomy of the scan data. The second 2D view 412 of scan data is provided from the 3D volume of scan data at an angle relative to the first 2D view 411 of scan data. In this embodiment, a third 2D view 413 of scan data, which is a sagittal view of a third portion of the bony anatomy of the scan data, is generated from the 3D volume of scan data and. The third 2D view 413 of scan data is provided from the 3D volume of scan data at an angle relative to the first 2D view 411 of scan data and relative to the second 2D view 412 of scan data. The first 2D view 411, the second 2D view 412 and the third 2D view 413 may be orthogonal relative to each other. The first 2D view 411, the second 2D view 412 and the third 2D view 413 may be activated in the same way as has been described with regard to FIGS. 5a-5b.

In this embodiment, a position object 414 comprises a line or cylinder. Hence, the position object may be three dimensional, but represented in each 2D view 411, 412, 412 in two dimensions only. The position object 414 can be introduced into the first 2D 411 view by first initiating a function for defining a second portion of the affected area, in this embodiment the affected femur shaft. The position of the position object 414 relative to the 3D volume of scan data provides positional information for the implant component. In this embodiment, the implant component is a femur implant for a hip implant. Once the function is initiated, the position object 414 can be positioned using the input device in the active 2D view, which may be the first 2D view 411, the second 2D view 412 or the third 2D view 413. When the position object 414 has been introduced into one of the 2D views, it may appear in the other 2D views, e.g. if it is a three-dimensional object represented by a 2D object in each 2D view. Hence, the position object 414 may first be introduced in one of the 2D views 411, 412, 413, and then the position of the position object 414 may be adjusted in any of the 2D views 411, 412, 413. Introducing the position object 414 in one of the 2D views 411, 412, 413 provides first positional information, and adjusting the position in any of the other 2D views provides second positional information. The first and/or the second positional information may comprise coordinate information in one or two dimensions. Hence, if the first and the second positional information only comprises information in one dimension, positional information in a third dimension may be necessary from a third 2D view. Together, the first positional information, the second positional information, and optionally the third positional information may provide coordinate information in three dimensions for the position object 414 relative to the 3D volume of scan data, as has been described above.

The position of the position object 414 can be adjusted in 3D space by adjusting its position in at least two of the 2D views 411, 412, 413, optionally three of the 2D views 411, 412, 413, depending on the degrees of freedom for adjusting its position in each 2D view 411, 412, 413. In the embodiment of FIGS. 6c-6d, the position of the position object can be adjusted in two dimensions in the first 2D view 411 and in only one dimension in the third 2D view 413, which is indicated by a four-way direction indicator 405a, and a two-way direction indicator 405b, respectively. The position of the position object 414 may also be adjusted in the third 2D view 413 if desired. However, this is not necessary but may be desired for more accurate adjustment of the position in in three dimensions. Hence, when the position of the position object 414 has been adjusted, the affected anatomy space has been defined. In this embodiment, the position object 414 is indicated with a circle in the second 2D view 412. In this embodiment, a line would be represented as a dot in a horizontal view, such as the second 2D view 412 when positioned to indicate a femur shaft in the first 2D view and third 2D view 413. This will be difficult do distinguish for the person performing the planning. Hence a circle 415 in the second 2D view 412, the centre of which indicates the position of the position object 414 in the first 2D view 411 and the third 2D view 413, indicates the position of the position object 414. Hence, objects having different shapes depending on in which 2D view they are displayed may represent the position object 414.

Figure 7A:
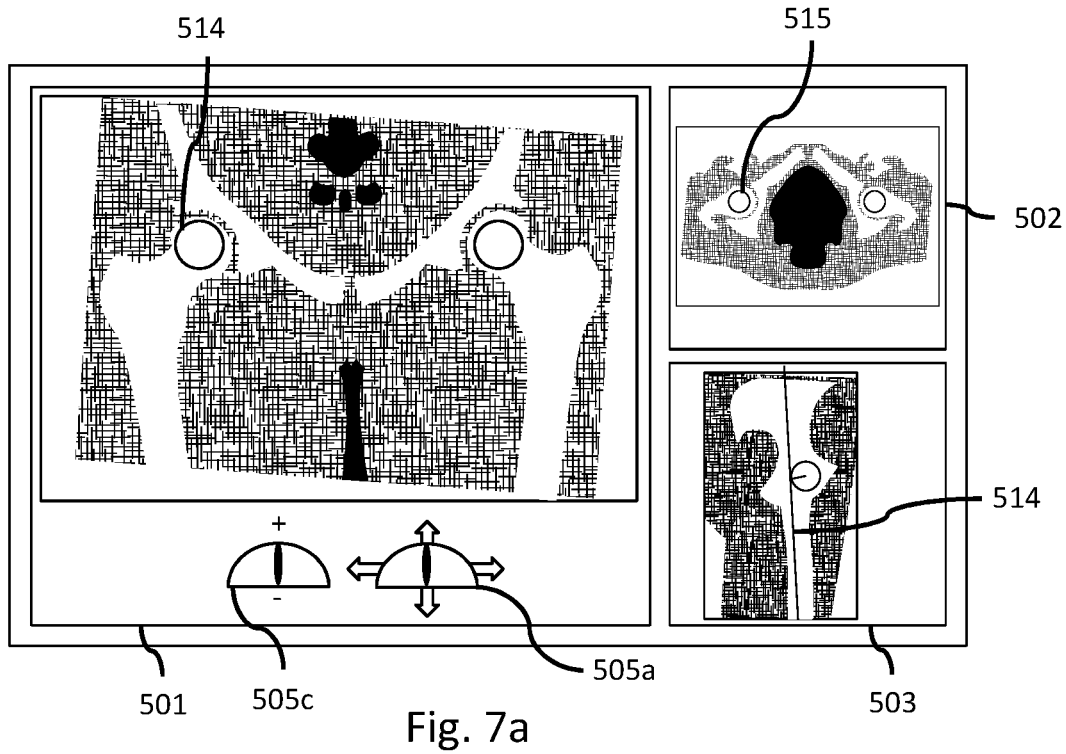
Figure 7B:
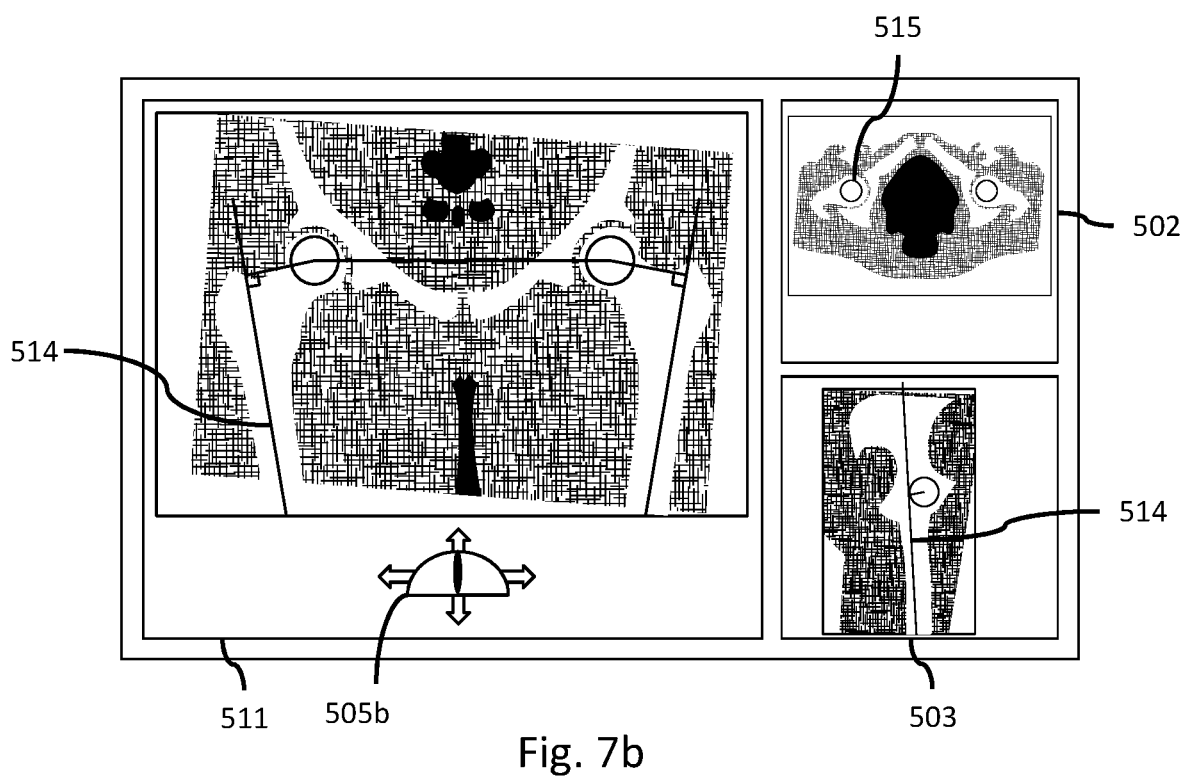

FIGS. 7a-7b further illustrate step 130 of FIG. 3, wherein the unaffected anatomy space is indicated displayed and positional information is defined for the implant component. The positional information provided with regard to the unaffected anatomy space can be used for calculation of offsets for the affected anatomy before and after surgery. In the illustrated embodiment, the unaffected anatomy is a hip joint, i.e. a femur head and shaft. The positional information for the unaffected anatomy space can be defined in the same way as has been described with regard to the affected anatomy space and in relation to FIGS. 6a-6d. Therefore, FIGS. 7a-7b will not be described in more detail here. The reference numerals of the elements in FIGS. 7a-7b correspond to similar reference numerals of the elements in FIGS. 6a-6d with only the first digit being replaced and are positioned for the unaffected anatomy space, and thus objects therefore. For example, reference numeral 401 corresponds to reference numeral 501, 402 to 502, 403 to 503, 405a-c to 505a-c, 411 to 511, 414 to 514, and 415 to 515.

Once the affected anatomy space and the unaffected anatomy space has been indicated, offset and LLD (Limb Length Discrepancy) can be generated based on the positional information defined in the multiple 2D views. The offset information may e.g. comprise acetabular/true femoral/functional femoral offset before (indicating offset of the affected anatomy) and unaffected acetabular acetabular/true femoral/functional femoral offset. These values may be based on the positions of the position indicators for the unaffected and affected anatomy, and be used for guiding the positioning of the implant component. The offsets and LLD information may be calculated as is generally known in the art. However, embodiments of the invention comprise defining the positions of the affected and unaffected anatomy in multiple 2D views of scan data generated form the same 3D volume of scan data. Since the position of the position indicators may be improved by the method according to embodiments of the invention, also the accuracy of the offset and LLD information may be improved, wherein also the positioning of the implant components may be improved and more accurate, wherein the outcome of the surgery may be improved and thus patient satisfaction.

The offsets may e.g. be defined as described in Acta Orthop. Belg., 2010, 76, 432-442 "Primary hip arthroplasty templating on standard radiographs A stepwise approach", by Thierry SCHEERLINCK. The femoral offset can be defined as the shortest distance between the femoral rotation centre and the longitudinal axis of the proximal femur. The longitudinal axis can be found by drawing a line between the middle of the projected femoral canal, measured at two different levels in a part of the proximal femur that appears to be symmetrical. If pathology has deformed the femoral head, the original femoral offset can be calculated as the distance between the original femoral rotation centre and the longitudinal axis of the proximal femur. The femoral offset is important because it controls the tension and moment arm of the abductor muscles, the tension of the soft tissues, the wear of the acetabular component and the load imposed on both, the acetabular and femoral implants. Failure to restore the femoral offset may lead to excessive wear, limping and/or hip instability. On the other hand, excessive femoral offset has the potential to overload the femoral implant, to generate micromotion at the implant-bone interface and to cause pain in the abductor muscles and the region of the greater trochanter. The acetabular offset can be defined as the shortest distance between the acetabular rotation centre and a perpendicular to the interteardrop line, drawn along the projection of the most distal part of the teardrop. If pathology has deformed the acetabulum, the original acetabular offset can be found in the same way, but replacing the hip rotation centre with the original acetabular rotation centre. The acetabular offset is important because it controls the tension of the abductor muscles and the soft tissues as well as the lever arm of the body weight and thus the load transmitted to the acetabulum. Decreasing the acetabular offset by excessive medialisation of the acetabular component may lead to limping and/or hip instability. Increasing the acetabular offset may overload the cup. These aspects can be reduced or eliminated by using embodiments of the planning method according to the invention.

Figure 8A:
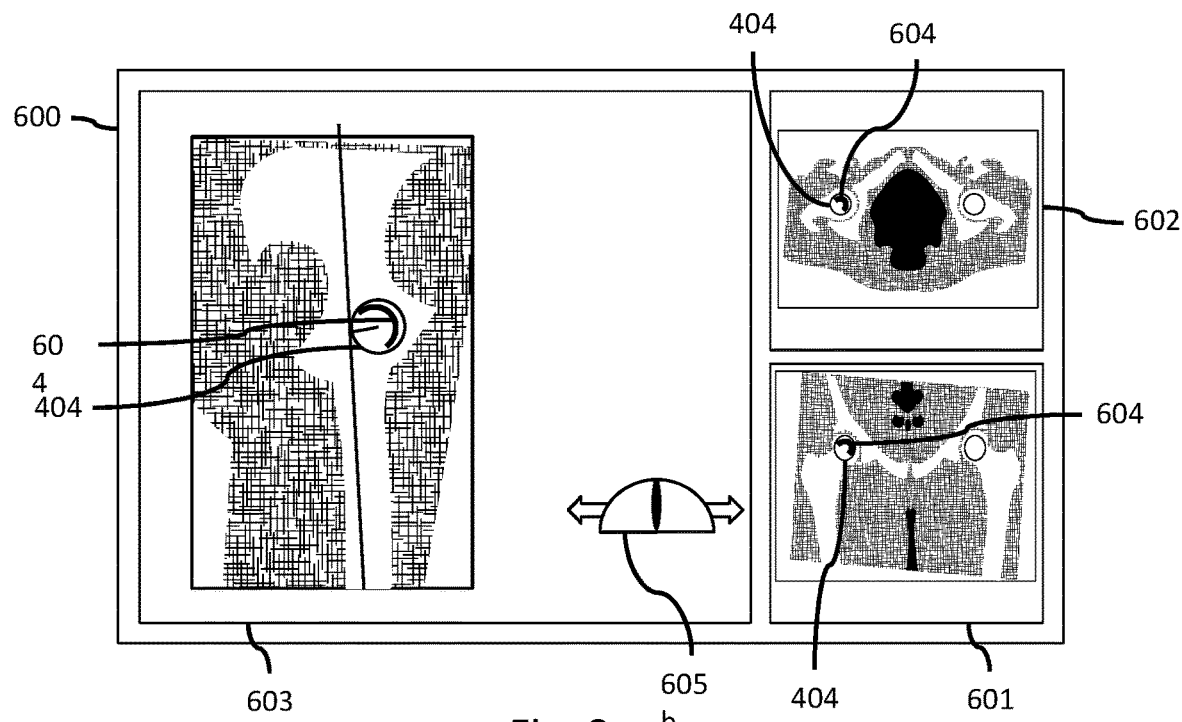
Figure 8B:
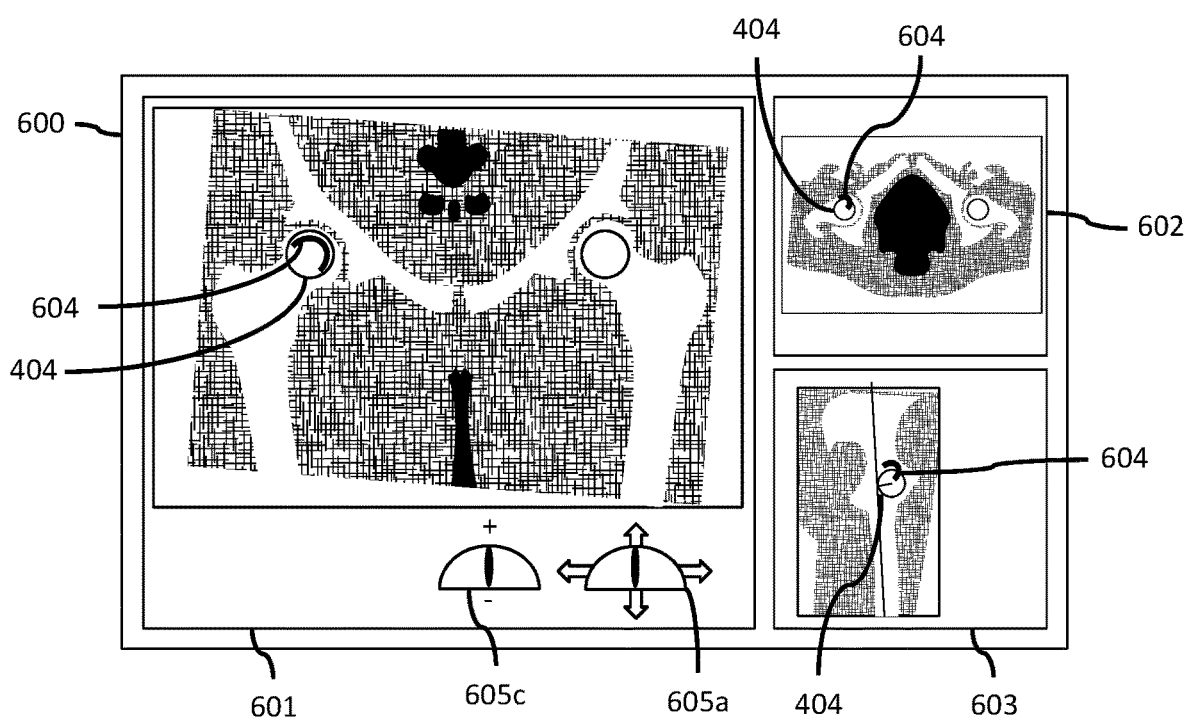
Figure 8C:
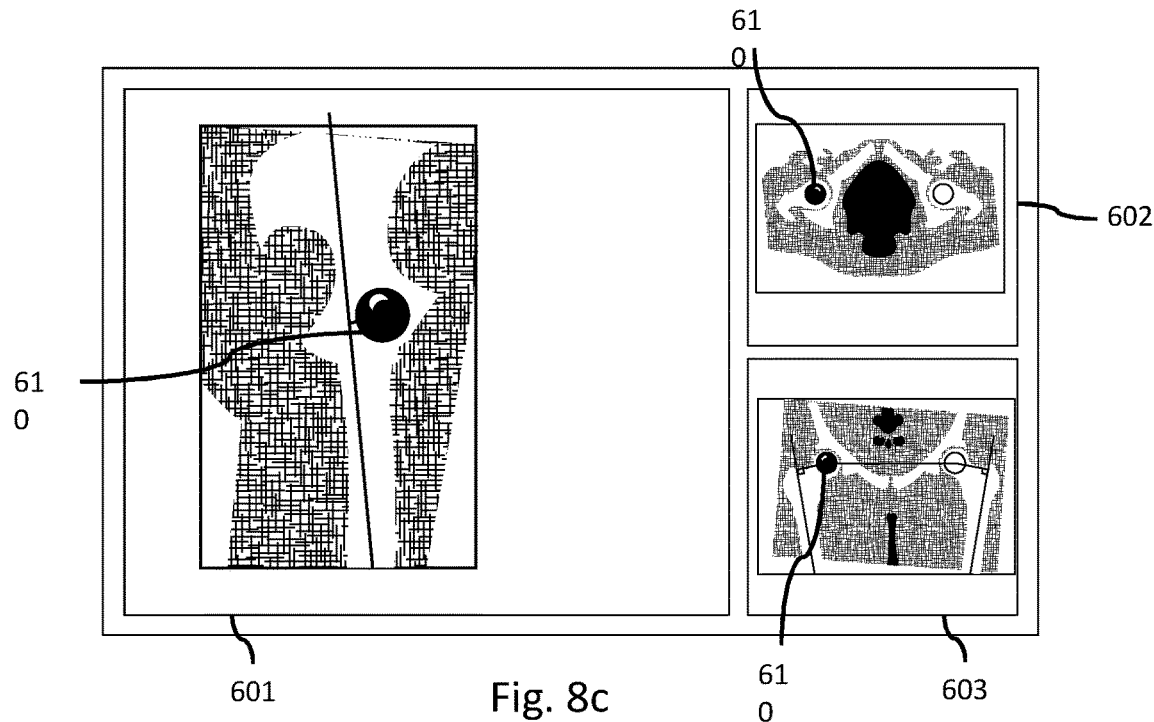

FIGS. 8a-8c further illustrate steps 140 and 150 of FIG. 3, wherein implant components are positioned based on the indications of the affected anatomies illustrated in FIGS. 6a-6d, and then the positions of which are adjusted in multiple 2D views for the correct positioning in 3D space and providing of 3D positional information.

FIG. 8a illustrates defining in display 600 positional information for a first implant component in a first 2D view 601, a second 2D view 602 and a third 2D view 603 of scan data comprising a first portion of the bony anatomy, and second portion of the bony anatomy, and a third portion of the bony anatomy, respectively, of the scan data, as has been described above with regard to FIGS. 5a-7b. The various 2D views 601, 602, 603 may be managed as has been described above, such as activated, defining positional information in one or two dimensions as is indicated by the direction indicators 605a, 605b, and size indicator 605c, and will therefore not be described in more detail with regard to FIGS. 8a-8c. Defining the positional information for the implant component may be done in multiple steps. In a first step, the positional information for the implant component may be defined in multiple 2D views of scan data. Then, in a second step a virtual 3D representation of the implant component may be overlaid in the 2D views, and then adjusted if necessary. An initial location of the implant component relative the 2D views of scan data may be based on the positional information for the affected anatomy, which is represented by the position object 404, which was defined in previous steps. In FIGS. 8a-8b, the location for the implant component has been indicated by a location object 604, in this embodiment a half-sphere with a radius slightly smaller than the radius of the position indicator 404 for the affected anatomy. The location object 604 can be introduced into the 2D views 601, 602, 603 by initiating a function for defining a first portion the affected area, in this embodiment the affected femur head. Once the function is initiated, the location object 604 may be automatically positioned based on the positional information of the position object 404 for the affected anatomy, such as within the boundary of the position object 404 as is illustrated in FIG. 8a. Then the position of the location object 604 may be adjusted in one or two dimensions at the time in multiple 2D views of scan data, which is illustrated in FIG. 8b. In FIG. 8b, the position of the location object 604 has been exaggerated in order to illustrate that the location object has been moved to a different position relative to its initial position relative to the position object 404, which is not its optimal position. However, the person performing the planning can manually adjust the position of the location object 604 using the input device as has been described above with regard to the position objects.

FIG. 8c illustrates defining the position of a virtual 3D implant component 610 relative to the 3D volume of scan data based on the position of the location object 604. As can be seen in FIG. 8c, the position of the virtual implant component 610 is based on the positional information defined by the position of the location object 604 relative to the 3D volume of scan data. The position of the virtual implant component may be adjusted in the same way as the location object 604 and the position object 404, as has been described above in one or two dimensions at the time in multiple 2D views in order to adjust its position in three dimensions relative the 3D volume of scan data. The positional information for the implant component may be based on the x/y/z coordinates of the location object.

The second implant component may be designed to fit the first implant component, such as a head of a femur component to a cup component. Hence, when the first implant component has been positioned, the position of the second implant component is partially provided by the position of the first implant component, such as the position of the head of the femur is provided by the position of the cup, but can be moved therein and therefore the stem can be partially determined by the user performing the planning.

Figure 9:
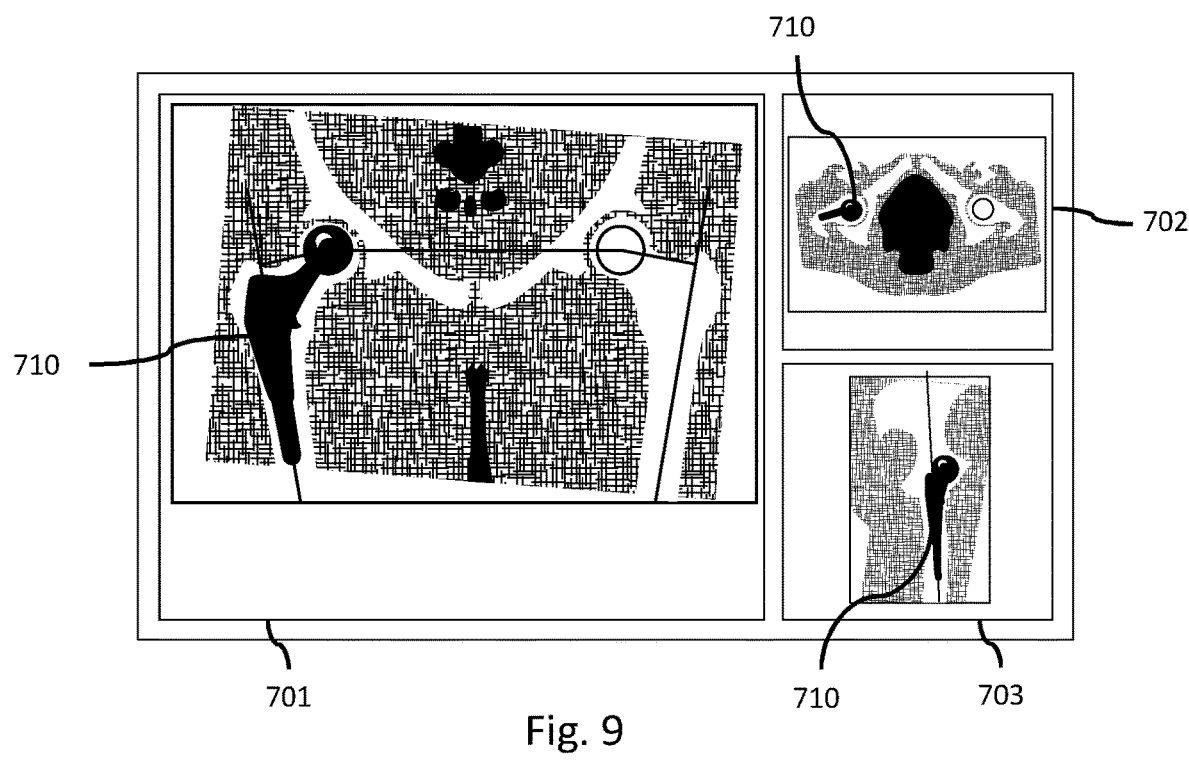

FIG. 9 illustrates positioning a second implant component 710, here in the form of an implant stem for a hip implant. The positional information for the second implant component 710 may be defined in a first 2D view of scan data 701, a second 2D view 702 of scan data, and a third 2D view 703 of scan data, as has been described above with regard to FIGS. 5a-8c. This may be done in multiple steps, by defining positional information for a location object, that may be represented in 2D and then introducing a virtual representation of the implant component, as has been described with reference to FIG. 8a-8c. Hence, what has been described with regard to previous embodiments, and especially to the embodiments of FIGS. 6a-6c, is applicable also to the embodiment of FIG. 9.

As has been discussed above, for at least one implant component first positional information may be defined relative to a first 2D view of scan data and second positional information may be defined relative to a second 2D view of scan data. Adjusting the position of objects relative to any of the 2D views may be locked to adjustment in a single direction or dimension. This may make the position easier, with enhanced position for the use of the positional information more accurate. In some embodiments, adjusting the position relative to any of the 2D views may be locked to adjustment in a two directions or dimensions. Hence, since the 2D views of scan data are generated based on the same volume of scan data that is aligned with the planning planes, it is possible to provide positional data for the implant component in three dimensions relative to the 3D volume of scan data using two or three 2D views generated from the scan data at an angle relative to each other. The number of views is dependent on the degrees of freedom—all three views locked to planning in a single dimension naturally requires three 2D views locked for providing positional information in a single separate dimensions each, such as an x-dimension in a first 2D view, y-dimension in a second 2D view, and a z-dimension in a third 2D view. Together, the coordinates provide x/y/z positional coordinate information for the virtual implant component relative to the 3D volume of scan data.

Figure 10:
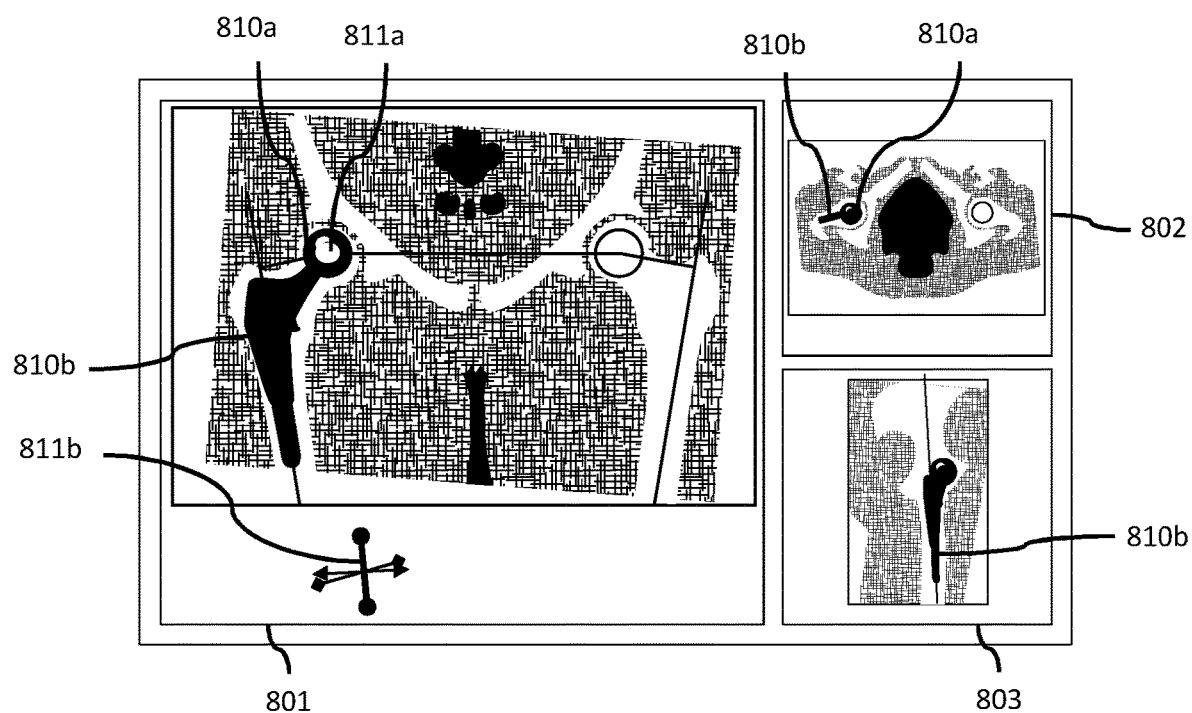

FIG. 10 illustrates an embodiment of Step 140 of FIG. 3, wherein positional information for a 3D representation of the virtual implant component 810a, 810b may first be provided by first and second positional information defined in multiple 2D views 801, 802, 803 of scan data as has been described above. A three-dimensional position adjustment object 811a, 811b is associated with each 3D representation of the virtual implant component 810a, 810b. Associated with a first 3D representation of the virtual implant is a first three-dimensional position adjustment object 811a, in this embodiment shaped as a sphere. The first implant component is a 3D representation of a cup for a hip implant. The cup does not have a particular axis, rather a center. The sphere may be positioned in the center in order to make adjustment of the position of the 3D representation of the implant component easy and efficient. Associated with a second 3D representation of the virtual implant component is a second three-dimensional position adjustment object 811b. In FIG. 10, the second three-dimensional position adjustment object 811b is illustrated separated from the implant component 810b. However, it may alternatively be associated therewith. In this embodiment, it comprises an axis indicator. The axis indicator is in this embodiment represented by a 3D cross-hair. The second implant component is a 3D representation of a stem of a hip implant. The stem has a longitudinal axis. The axis indicator may have one axis aligned with the longitudinal axis of the second implant component. Movement of the axis indicator can be locked to movement in one dimension at the time. Selecting one of the axis of the axis indicator may be done by drag-and-drop functionality, i.e. indicating the axis holding an activation button of the mouse, moving the input device, and releasing the activation button. Hence, moving one of the axes of the axis indicator at the time and in only one dimension at the time, is possible. In some embodiment, each axis may be moved in two dimensions at the time, such as in a plane parallel to a corresponding 2D view of scan data 801, 802, 803. Furthermore, in some embodiments, activating an axis of the axis indicator also activates an associated 2D view of scan data, which e.g. may be enlarged and/or shift position upon activation of movement of the position of the implant component 811a, 811b. Hence, the dimension in which each axis of the axis indicator is moveable may be a plane parallel to at least one of 2D views of scan data 801, 802, 803. Hence, the axis indicator may comprise a set of indicators, such as a first, second and third axis indicator associated with the virtual implant component and being moveable in a single dimension each. The 3D representation of the virtual implant component 811a, 811b may be moved in a single dimension at the time by moving one of the first, second or third axis indicators.

Once the positional information for one or several implant components has been obtained, it may be used for various purposes, wherein enhanced positional information is of importance. In some embodiments, the positional information for the implant component is used for dividing the 3D volume of scan data into a first 3D sub-volume of scan data and at least a second sub-volume of scan data based on the first and second positional information, and optionally third positional information, obtained from at least two 2D Views of scan data. Optionally it may also be based on at least a section of the virtual implant component. At the positions where the implant component has been defined, surfaces of the implant component may be used for separating the scan data into the sub volumes. This may e.g. be at the positions wherein a surface of implant component 811a is located, such as the half-spherical surface of the cup for a hip implant, such as represented by a triangulated surface. Once separate sub-volumes are provided, they may be used to simulate movement of various parts of the scan data and thus simulate the outcome of the surgery. For example, scan data comprising bony anatomy relating to the pelvis may be separated into a first sub-volume and scan data relating to a leg may be separated into a second sub-volume. The position of a first implant component 811a, may be fixed relative to the first sub-volume, and the position of a second implant component 811b may be fixed relative to the second sub-volume. Movement of the second implant component 811b relative to the first implant component 811a may then be simulated, wherein the sub-volumes of data will also move relative to each other. If during the simulation the surgeon discovers that any of the implant components 811a, 811b, is located in a sub-optimal position, the positional information related thereto may be updated, and a new simulation performed if necessary. In some embodiments, the bony anatomies of the sub-volumes are rendered as 3D surface objects using volume rendering techniques.

In some embodiments, the positional information for the implant component is used for surgical navigation, wherein a position of first virtual implant component relative to the 3D scan data is based on the first and the second positional information. A second virtual implant component, which is a virtual representation of the position of an actual implant relative to the actual bony anatomy of the patient, which is tracked using a surgical navigation system, may also be displayed on the screen relative to the first virtual implant component.

Figure 11:
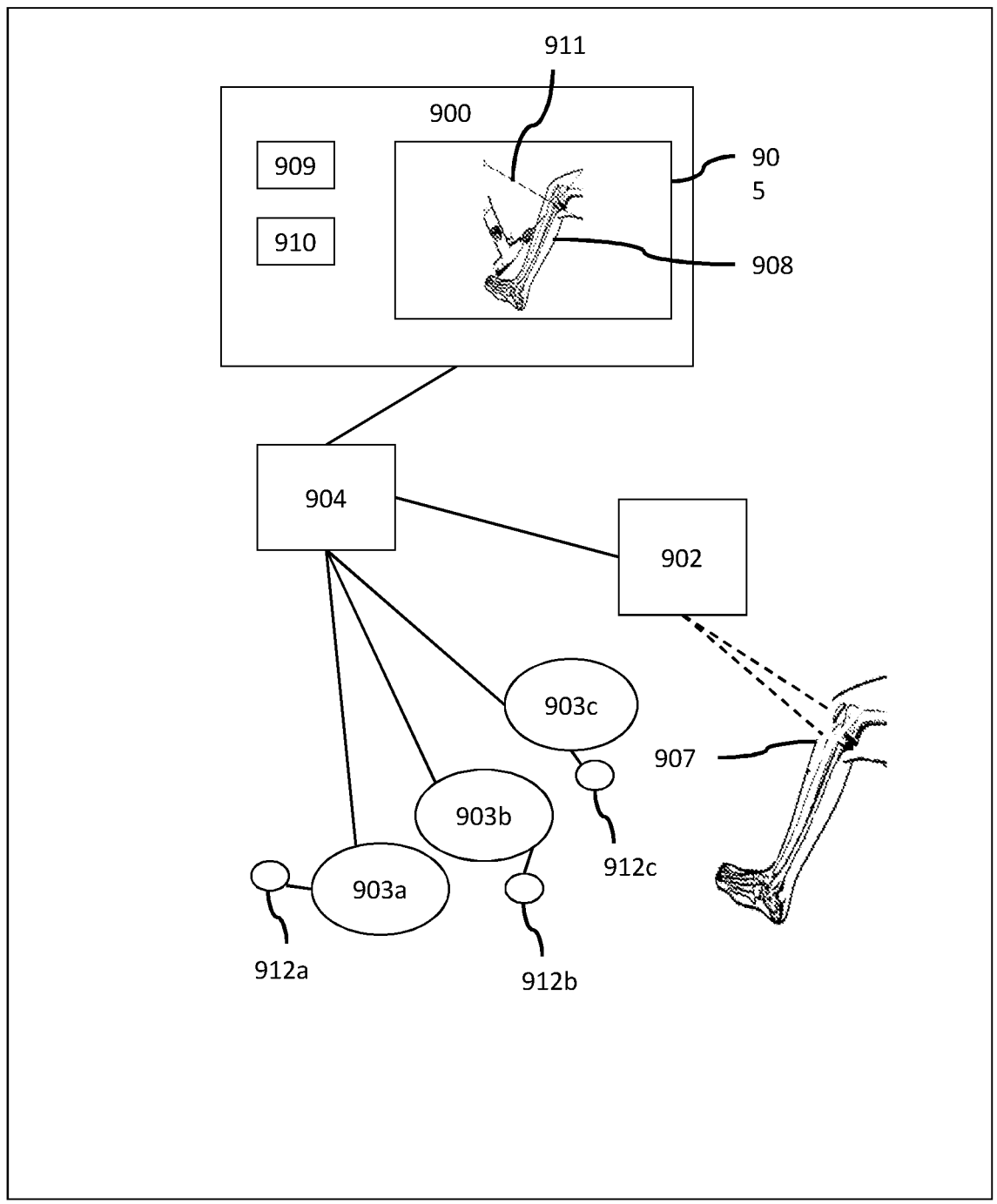
FIG. 11 is a schematic view of a surgical navigation system in which embodiments of the invention are integrated.

FIG. 11 illustrates a surgical navigation system, in which the planning method described above may be used. A planning unit 900 may comprise a computer having software code segments for providing the pre-operative plan. As such, the planning unit 900 may have one or several input devices 909, such as a keyboard and a mouse, and one or several output devices, such as a display 910. Using the patient scan data and a virtual representation of the patient 908, the pre-operative plan may be made using multiple 2D views of the scan data as has been described above. The pre-operative plan may comprise planning at least one position and orientation of surgical object 903a, 903b, 903c relative to the patient structure 907, such as a bony anatomy during the surgery. In some embodiments, the surgical object 903a, 903b, 903c comprises the virtual implant. Hence, the pre-operative plan may comprise positioning and orienting a virtual representation of the surgical object, referred to as a virtual object 911, to an optimal position and orientation relative to at least one virtual structure 908, such as the bony anatomy of the scan data. An example embodiment would be to position a hip implant relative the femur and orient the head of the hip implant relative to the acetabulum of the pelvis. In relation to a hip replacement, the surgical object, and thus the virtual object, may comprise both the acetabular cup and the femoral component. Thus the pre-operative plan may comprise planning multiple surgical objects, 903a, 903b, 903c, such as the acetabular cup and the femoral component via their virtual representations relative to multiple patient structures, such as the femur and acetabulum. In the embodiment of FIG. 11, planning of a knee surgery is disclosed, wherein the patient structure and the virtual representation thereof may comprise multiple structures, such as the femur tibia, fibula, and/or patella. In this embodiment, the surgical object 911 comprises a surgical instrument, and planned positions and orientations thereof, and thus positional information thereof. The surgical object 903a, 903b, 903c is moveable relative to the patient structure during surgery.

The planning unit 900 is adapted to provide the pre-operative plan including planned position and orientation of the virtual object relative to of the virtual structure using multiple 2D views as has been described above. Also, the planning unit 900 may be adapted to register the patient structure to the virtual structure 908 and the surgical object 911 to the virtual object 908.

The system provides feedback of at least one surgical object 903a, 903b, 903c relative the pre-operative plan. The pre-operative plan includes the virtual object 911, which is the virtual representation of the surgical object, and a virtual structure 908, which is the virtual representation of the patient structure. The virtual object 911 and the virtual structure 908 may be represented as 3D objects, such as 3D surface objects. Hence the planning unit 911 may be a 3D planning unit wherein the position in space is defined using multiple 2D views as has been described above.

The position registration unit 902 is according to embodiments adapted to obtain at least one position of the patient structure. The position registration unit 902 may operate without any fiduciary markers present in the scan data as well as during surgery. Hence, the patient does not have to go through any operation to place the fiduciary markers before the surgery. Instead, the position registration unit 902 may operate based on the surface of the patient structure, such as the shape thereof, positions of the surface within a coordinate system of the position registration unit 902, etc., as will be discussed further below. The position registration unit 902 may also be adapted to register the position and orientation of the surgical object 903a, 903b, 903c.

A tracking unit 912a, 912b, 912c, which may be attached to the surgical object 903a, 903b, 903c, is adapted to track a current position and orientation of the surgical object 903a, 903b, 903c within a coordinate system and thus relative to the patient structure when they are provided within the same coordinate system or coordinate systems that are registered. The communication hub 904 is adapted to communicate position data from the position registration unit 902 to the planning unit 900, and position and orientation data from the tracking unit 912a, 912b, 912c to the planning unit 900. Hence, the position of the patient structure 907 can be registered by the position registration unit 902 and relayed to the planning unit 900, and registered to the patient structure. Similarly, the position of the surgical object 903a, 903b, 903c can be registered, such as by the registration unit 902 or via docketing station as will be disclosed below, and its position and orientation continuously tracked by the tracking unit 912a, 912b, 912c, and relayed back to the planning unit 900 via the communication hub 904. Furthermore, in some embodiments, the position registration unit 902 is adapted to dynamically update the position and orientation of the patient structure 907. Hence, the communication hub 904 communicates data to and from the various units in the system. The planning unit may update the position of the virtual object 911 relative the virtual structure 908 based on the tracked position and orientation of the surgical object 903a, 903b, 903c in the coordinate system of the position registration unit 902 or the patient depending on how the system is set up.

In embodiments of the invention, a feedback device 905 is adapted to provide feedback of the current position and orientation of the surgical object 903a, 903b, 903c relative to the planned position and orientation of the virtual object 911 in response to the tracked current position and orientation of the surgical object 903a, 903b, 903c. In some embodiments, the feedback comprises a visual indicator. A visual indicator may e.g. comprise a display, a light emitter, such as one or several LEDs, etc. In the embodiment of FIG. 11, the feedback device 903 is a display of the planning unit 900. Hence, the display may render the virtual structure 908, a representation of the virtual object 911 in its planned position(s) and orientation(s) relative the virtual structure 908, and a representation of the current position and orientation of the surgical object 903a, 903b, 903c relative to the patient structure 907. The representation of the current position and orientation of the surgical object 903a, 903b, 903c relative to the patient structure 907 may e.g. be provided by a virtual 3D model of the surgical object 903a, 903b, 903c. Hence, the visual indicator 905 may be adapted to provide visual feedback of current position and orientation of the virtual object relative to the planned orientation and position of the virtual object based on the tracked current position and orientation of the surgical object. This may e.g. be provided via a display. The visual indicator may be provided at the surgical object, such as integrated therewith, for example within a single chassis of the surgical object. Alternatively or additionally, the visual indicator may be adapted to provide visual indication of the deviation of the current position and orientation of the virtual object relative the planned position and orientation of the virtual object on a screen, and thus between the current position and orientation of the surgical object and its planned position and orientation. This may be provided based on or in response to the tracked current position and orientation of the surgical object. Some embodiments may also comprise a visual indicator adapted to provide visual indication of the deviation of the current position and orientation of the surgical object relative the planned position and orientation of the virtual object, such as via a visual indicator integrated with the surgical object. For example, a multi-colour LED may indicate the deviation from one or several positions and orientations, such as red indicating >50 mm from planned position and orientation, yellow indicating the range 49 mm< >10 mm from planned position and orientation, and green indicating <10 mm from planned position and orientation. Alternatively, the ranges may be indicated using a single colour flashing LED, with different flashing pattern depending on the deviation. In still other embodiments, the feedback device 90 may be acoustic, wherein the pitch, type of signal, etc. of the acoustic signal would indicate the ranges. An acoustic feedback may complement or replace the other embodiments for providing feedback.

The positional information regarding any of the implant components may be exported to the navigation unit for guiding the position of the actual implant relative to the bony anatomy of the patient.

According to embodiments of the invention, the positional data defined using multiple 2D views of scan data may be used to plan a surgical template and produce a surgical template. Planning using multiple 2D views of scan data has the advantage that the surgical template may accurately fit the object against which it is designed to fit. The surgical template may also be a surgical object in itself and be integrated with a surgical navigation system, as has been discussed above.

The processes and systems described herein may be performed on or encompass various types of hardware, such as computer systems. In some embodiments, computer, display, and/or input device, may each be separate computer systems, applications, or processes or may run as part of the same computer systems, applications, or processes—or one of more may be combined to run as part of one application or process—and/or each or one or more may be part of or run on a computer system. A computer system may include a bus or other communication mechanism for communicating information, and a processor coupled with the bus for processing information. The computer systems may have a main memory, such as a random access memory or other dynamic storage device, coupled to the bus. The main memory may be used to store instructions and temporary variables. The computer systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor. Communication among modules, systems, devices, and elements may be over a direct or switched connection, and wired or wireless networks or connections, via directly connected wires, or any other appropriate communication mechanism. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, secure sockets, VPN, encrypted or unencrypted pipes, MIME, SMTP, MIME Multipart/Related Content-type, SQL, etc.

Any appropriate 3D graphics processing may be used for displaying or rendering including processing based on OpenGL, Direct3D, Java 3D, etc. Whole, partial, or modified 3D graphics packages may also be used, such packages including 3DS Max, SolidWorks, Maya, Form Z, Cybermotion 3D, or any others. In some embodiments, various parts of the needed rendering may occur on traditional or specialized graphics hardware. The rendering may also occur on the general CPU, on programmable hardware, on a separate processor, be distributed over multiple processors, over multiple dedicated graphics cards, or using any other appropriate combination of hardware or technique.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process, such as functions referred to above. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

The invention claimed is:

1. A computer-implemented method for positioning a virtual implant component relative to a volume of scan data of a patient, said method comprising:
receiving a 3D volume of scan data of a patient, said scan data of a patient comprising scan data representing a bony anatomy of the patient;
storing the 3D volume of scan data in a memory;
transforming at least a portion of the 3D volume of scan data stored in a memory into multiple 2D views each showing a portion of said bony anatomy, said transforming comprising:
generating, with a processor, a first 2D view of scan data based on the 3D volume of the scan data of the patient,
generating, with the processor, a second 2D view of scan data based on the 3D volume of scan data, wherein the second 2D view of scan data is provided from the 3D volume of scan data at an angle relative to the first 2D view of scan data, and
generating, with the processor, a third 2D view of scan data based on the 3D volume of scan data, wherein the third 2D view of scan data is provided from the 3D volume of scan data at an angle relative to the first 2D view of scan data and the second 2D view of scan data;
storing in a memory and displaying said first, second and third 2D views of scan data on a graphical user interface;
receiving in a memory first positional information for the virtual implant component relative to the first 2D view of scan data input through the graphical user interface displaying the first 2D view of scan data, said first positional information having a maximum of two degrees of freedom-;
receiving in a memory second positional information for the virtual implant component relative to the second 2D view of scan data input through the graphical user interface displaying the second 2D view of scan data, said second positional information having a maximum of two degrees of freedom;
receiving in a memory third positional information for the virtual implant component relative to the third 2D view of scan data input through the graphical user interface displaying the third 2D view of scan data, said third positional information having a maximum of two degrees of freedom;
combining, with the processor, the first positional information, the second positional information, and the third positional information to create 3D positional information for the virtual implant component relative to the 3D volume of scan data, wherein the combination of the first positional information, the second positional information, and the third positional information comprises positional information for three different dimensions; and
displaying, in the graphical user interface, a 3D representation of the virtual implant component in a position relative to a 3D representation of the patient anatomy as defined by the 3D positional information.

2. The method according to claim 1, comprising adjusting, through said graphical user interface, a position of at least one of:
an object relative to the first 2D view of scan data for generating the first positional information,
an object relative to the second 2D view of scan data for generating the second positional information, and
an object relative to the third 2D view of scan data for generating the third positional information,
wherein said adjusting is locked, according to instructions stored in memory and executed by the processor, to adjustment in a single dimension in each of said 2D views of scan data.

3. The method according to claim 1, wherein displaying said first, second and third 2D views of scan data comprises:
separately displaying said first, second and third 2D views of scan data in the graphical user interface; and
said method further comprises displaying, in the graphical user interface, a position adjustment object associated with the virtual implant component, the position adjustment object being moveable in a single dimension at a time, wherein each dimension is parallel to at least one of the first and the second 2D views of scan data.

4. The method according to claim 1, wherein, said receiving of said first, second, and third positional information for the virtual implant component comprises a user defining through the graphical user interface positional information for at least one of: an affected femoral head, affected femoral shaft, unaffected femoral head, unaffected femoral shaft, a cup of the virtual implant, a stem of the virtual implant, and a knee implant, and storing in memory said user defined positional information.

5. The method according to claim 1, further comprising dividing, with the processor according to instructions stored in memory, the 3D volume of scan data into a first 3D sub-volume of scan data and a second sub-volume of scan data based on the combination of the first, second and third positional information.

6. The method according to claim 1, further comprising displaying, in a graphical user interface, a first virtual implant component in a position relative to a 3D representation of the patient anatomy based on the first, the second, and the third positional information, and a second virtual implant component, which is a virtual representation of the position of an actual implant relative to the actual bony anatomy of the patient.

7. The method according to claim 1, comprising exporting navigational data based on the first, second, and third positional information to a navigation unit for guiding the position of an actual implant relative to the actual bony anatomy of the patient.

8. The method according to claim 1, wherein said steps of generating the first 2D view of scan data, the second 2D view of scan data, and the third 2D view of scan data comprises providing the first, second and third 2D views of scan data, with the processor according to instructions stored in memory, by reformatting and/or reconstructing slices from the 3D volume of scan data.

9. The method according to claim 8, wherein at least one of the second 2D view of scan data, and the third 2D view of scan data is provided by the processor from the 3D volume of scan data stored in memory at an angle relative to the first 2D view of scan data that is orthogonal.

10. The method according to claim 1, wherein the first positional information is defined in the dimensions of the first 2D view of scan data, the second positional information is defined in the dimensions of the second 2D view of scan data, and the third positional information is defined in the dimensions of the third 2D view of scan data.

11. The method according to claim 1, further comprising separately displaying in the graphical user interface the first 2D view of scan data, the second 2D view of scan data, and the third 2D view of scan data.

12. The method according to claim 1, comprising adjusting at least one of the first positional information relative to the first 2D view of scan data, the second positional information relative to the second 2D view of scan data, and the third positional information relative to the third 2D view of scan data.

13. The method according to claim 12, wherein the adjusting at least one of the first positional information, the second positional information, and the third positional information for the virtual implant component is guided by an offset for an affected anatomy relative to an unaffected anatomy.

14. The method according to claim 1, comprising defining each of the first positional information, the second positional information, and the third positional information to comprise coordinate information in one dimensions, wherein the combination of the first positional information, the second positional information, and the third positional information comprises coordinate information in three different dimensions.

15. The method according to claim 2, wherein said at least one object comprises at least one of a virtual representation of an implant component and a virtual representation of a template for sizing an implant.

16. Computer system comprising a programmable device configured to perform the method of claim 1.

17. A computer program product stored on a non-transitory computer readable medium, comprising: computer readable program code segments for causing a computer to execute the method of claim 1.

18. A computer-implemented method for positioning and displaying a virtual implant component relative to a 3D volume of scan data representing a patient structure, comprising:
displaying first, second and third 2D views of scan data within a graphical user interface on a computer screen, wherein said 2D views are based on the 3D volume of scan data, wherein the second 2D view of scan data is provided by a processor from the 3D volume of scan data at an angle relative to the first 2D view of scan data, and the third 2D view of scan data is provided by the processor from the 3D volume of scan data at an angle relative to the first 2D view of scan data and the second 2D view of scan data;
receiving first positional information for the virtual implant component relative to the first 2D view of scan data through the graphical user interface displaying the first 2D view of scan data, said first positional information having a maximum of two degrees of freedom;
receiving second positional information for the virtual implant component relative to the second 2D view of scan data through the graphical user interface displaying the second 2D view of scan data, said second positional information having a maximum of two degrees of freedom;
receiving third positional information for the virtual implant component relative to the third 2D view of scan data through the graphical user interface displaying the third 2D view of scan data, said third positional information having a maximum of two degrees of freedom; and
displaying a 3D representation of the virtual implant component within the graphical user interface relative to a 3D representation of the patient anatomy in a position defined by the first and second positional information, wherein said 3D representation is provided by the processor based on a combination of said first, second and third positional information, and comprises positional information for three different dimensions.

19. The method according to claim 18, further comprising:
displaying within the graphical user interface at least one virtual object relative to at least one of the first, second, and third 2D views of scan data; and
adjusting, through said graphical user interface, a position of at least one of an object relative to the first 2D view of scan data,
an object relative to the second 2D view of scan data, and
an object relative to the third 2D view of scan data,
wherein said adjusting is locked by the processor to adjustment in a single dimension in each of said 2D views of scan data.

20. The method according to claim 18, further comprising displaying a position adjustment object associated by the processor with the virtual implant component, the position adjustment object being moveable within the graphical user interface in a single dimension at a time, wherein each dimension is parallel to at least one of the first and the second 2D views of scan data.

21. The method according to claim 18, wherein, said receiving of said first, second, and third positional information for the virtual implant component comprises a user defining through the graphical user interface positional information for at least one of: an affected femoral head, affected femoral shaft, unaffected femoral head, unaffected femoral shaft, a cup of the virtual implant, a stem of the virtual implant, and a knee implant.

22. The method according to claim 18, comprising displaying the 3D volume of scan data in the graphical user interface as a first 3D sub-volume of scan data and a second 3D sub-volume of scan data provided by the processor based on the combination of the first, second and third positional information.

23. The method according to claim 18, further comprising displaying in the graphical user interface a first virtual implant component in a position relative to the 3D volume of scan data provided by the processor based on the first, the second, and the third positional information, and a second virtual implant component, which is a virtual representation provided by the processor of the position of an actual implant relative to the actual bony anatomy of the patient.

24. The method according to claim 18, further comprising exporting navigational data based on the first, second, and third positional information to a navigation unit for guiding the position of an actual implant relative to the actual bony anatomy of the patient.

25. The method according to claim 18, wherein said displaying the first, second and third 2D views of scan data comprises displaying said 2D views comprising images that have been at least one of reformatted or reconstructed by the processor from the 3D volume of scan data.

26. The method according to claim 25, wherein at least one of the second 2D view of scan data, and the third 2D view of scan data is displayed within the graphical user interface at an angle relative to the first 2D view of scan data that is orthogonal.

27. The method according to claim 18, wherein the first positional information is defined in the dimensions of the first 2D view of scan data, the second positional information is defined in the dimensions of the second 2D view of scan data, and the third positional information is defined in the dimensions of the third 2D view of scan data.

28. The method according to claim 18, further comprising separately displaying the first 2D view of scan data, the second 2D view of scan data, and the third 2D view of scan data.

29. The method according to claim 18, further comprising adjusting, through the graphical user interface, at least one of the first positional information relative to the first 2D view of scan data, the second positional information relative to the second 2D view of scan data, and the third positional information relative to the third 2D view of scan data.

30. The method according to claim 29, wherein the adjusting at least one of the first positional information, the second positional information, and the third positional information for the virtual implant component is guided by an offset for an affected anatomy relative to an unaffected anatomy.

31. The method according to claim 18, comprising defining each of the first positional information, the second positional information, and the third positional information to comprise coordinate information in one dimension, wherein the combination of the first positional information, the second positional information, and the third positional information comprises coordinate information in three different dimensions.

32. A computer-implemented method for positioning a virtual implant component relative to a 3D volume of scan data of a patient stored in a memory, the stored scan data including scan data representing a boney anatomy of the patient, said method comprising:
  generating, with a processor, a first 2D view of scan data based on the stored 3D volume of the scan data;
  generating, with the processor, a second 2D view of scan data based on the stored 3D volume of scan data, wherein the second 2D view of scan data is provided by the processor from the 3D volume of scan data according to instructions stored in memory at an angle relative to the first 2D view of scan data;
  separately displaying each of said first and second 2D views of scan data within a graphical user interface;
  receiving, in memory user input through the graphical user interface displaying the first 2D view of scan data, first positional information for the virtual implant component relative to the first 2D view of scan data, said first positional information limited by the processor to a maximum of two degrees of freedom;
  receiving, in memory user input through the graphical user interface displaying the second 2D view of scan data, second positional information for the virtual implant component relative to the second 2D view of scan data, said second positional information limited by the processor to a maximum of two degrees of freedom;
  combining said first positional information and said second positional information with the processor to position the virtual implant component relative to the 3D volume of scan data and generate 3D positional information for the virtual implant component including three different dimensions;
  storing the 3D positional information for the virtual implant component in memory;
  displaying a 3D representation of the virtual implant component within the graphical user interface separately relative to each of the first and second 2D views of scan data, in a position defined by said 3D positional information; and
  displaying a position adjustment object with the graphical user interface relative to each of said first and second 2D views of scan data, said position adjustment object associated with the virtual implant component and being moveable in a single orthogonal dimension at a time within each of the displayed first and second 2D views of scan data.

33. The method according to claim 32, further comprising adjusting, through said graphical user interface, a position of at least one of:
  an object relative to the first 2D view of scan data for generating the first positional information, and
  an object relative to the second 2D view of scan data for generating the second positional information,
  wherein said adjusting is locked according to instructions stored in memory and executed by the processor to adjustment in a single dimension in each 2D view of scan data.

34. The method according to claim 32, further comprising;
  displaying, in the graphical user interface, a third 2D view of scan data generated from the 3D volume of scan data, wherein the third 2D view of scan data is provided from the 3D volume of scan data at an angle relative to the first 2D view of scan data and the second 2D view of scan data, and wherein the first 2D view of scan data comprises a first portion of the bony anatomy, the second 2D view of scan data comprises a second portion of the bony anatomy, and the third 2D view of scan data comprises a third portion of the bony anatomy;
  defining, according to instructions stored in memory and executed by the processor, relative to the third 2D view of scan data third positional information for the virtual implant component; and
  providing 3D positional information for the virtual implant component relative to the 3D volume of scan data by combining with the processor according to instructions stored in memory the first positional information, the second positional information, and the third positional information.

35. The method according to claim 32, wherein defining first and second positional information for the virtual implant component comprises defining positional information for at least one of an affected femoral head, affected femoral shaft, unaffected femoral head, unaffected femoral shaft, a cup of the virtual implant, a stem of the virtual implant, and a knee implant.

36. The method according to claim 32, further comprising dividing, with the processor according to instructions stored in memory, the 3D volume of scan data into a first 3D sub-volume of scan data and a second sub-volume of scan data based on the combination of the first and second positional information.

37. The method according to claim 32, further comprising displaying in the graphical user interface a first virtual implant component in a position relative to a 3D representation of the patient anatomy based on the first and the second positional information, and a second virtual implant component, which is a virtual representation of the position of an actual implant relative to the actual bony anatomy of the patient.

38. The method according to claim 32, further comprising exporting navigational data based on the first and second positional information to a navigation unit for guiding the position of an actual implant relative to the actual bony anatomy of the patient.

39. The method according to claim 32, wherein generating the first 2D view of scan data, and the second 2D view of scan data comprises providing the first and second 2D views of scan data, with the processor according to instructions stored in memory, by reformatting and/or reconstructing slices from the 3D volume of scan data.

40. The method according to claim 39, wherein the second 2D view of scan data is provided by the processor from the 3D volume of scan data at an angle relative to the first 2D view of scan data that is orthogonal.

41. The method according to claim 32, wherein defining the first positional information and the second positional information for the virtual implant component through the graphical user interface is restricted by the processor according to instructions stored in memory to defining in a single degree of freedom for at least one of the first positional information and the second positional information.

42. The method according to claim 32, wherein the first positional information is defined in the dimensions of the first 2D view of scan data and the second positional information is defined in the dimensions of the second 2D view of scan data.

43. The method according to claim 32, further comprising adjusting at least one of the first positional information relative to the first 2D view of scan data, and the second positional information relative to the second 2D view of scan data.

44. The method according to claim 43, wherein the adjusting at least one of the first positional information and the second positional information for the virtual implant component is guided by an offset for an affected anatomy relative to an unaffected anatomy.

45. The method according claim 34, wherein defining the third positional information for the virtual implant component through the graphical user interface is restricted by the processor according to instructions stored in memory to defining a maximum of two degrees of freedom for the third positional information.

\* \* \* \* \*